(12) United States Patent
Fijalkowski et al.

(10) Patent No.: US 9,651,595 B2
(45) Date of Patent: May 16, 2017

(54) CELL AND METHOD FOR ELECTRICAL MEASUREMENTS OF HIGHLY REACTIVE POWDER AND LIQUID SAMPLES

(71) Applicant: UNIWERSYTET WARSZAWSKI, Warsaw (PL)

(72) Inventors: Karol Jan Fijalkowski, Warsaw (PL); Rafal Jurczakowski, Brwinów (PL)

(73) Assignee: UNIWERSYTET WARSZAWSKI, Warsaw (PL)

(*) Notice: Subject to any disclaimer, the term of this patent is extended or adjusted under 35 U.S.C. 154(b) by 284 days.

(21) Appl. No.: 14/353,023

(22) PCT Filed: Oct. 22, 2012

(86) PCT No.: PCT/IB2012/002111
§ 371 (c)(1),
(2) Date: Apr. 19, 2014

(87) PCT Pub. No.: WO2013/057574
PCT Pub. Date: Apr. 25, 2013

(65) Prior Publication Data
US 2014/0285221 A1    Sep. 25, 2014

(30) Foreign Application Priority Data
Oct. 21, 2011  (PL) .......................... 396725

(51) Int. Cl.
*G01R 27/22* (2006.01)
*G01N 27/02* (2006.01)
*G01N 27/22* (2006.01)

(52) U.S. Cl.
CPC ........... *G01R 27/22* (2013.01); *G01N 27/026* (2013.01); *G01N 27/226* (2013.01)

(58) Field of Classification Search
CPC .... G01N 27/026; G01N 27/226; G01N 27/07; G01N 27/235; G01N 27/264;
(Continued)

(56) References Cited

U.S. PATENT DOCUMENTS 2,913,609 A * 11/1959 Lennard ................ H01J 7/24
                                                             313/31
3,661,010 A *  5/1972 Neuwelt ............... G01N 27/404
                                                            204/409
(Continued)

FOREIGN PATENT DOCUMENTS

CN        2135137 Y    6/1993
CN        2141899 Y    9/1993

OTHER PUBLICATIONS

Trajans-Column.org, Scenes I-XXI, p. 6 [online], [retrieved on Mar. 23, 2016]. Retrieved from the Internet , <URL: http://www.trajans-column.org/?flagallery=trajans-column-scenes-xxi-1-21>.*
(Continued)

*Primary Examiner* — Julian Huffman
*Assistant Examiner* — Michael Konczal
(74) *Attorney, Agent, or Firm* — STLGip, P.C.

(57) ABSTRACT

The invention refers to a chamber for measurements of electrical properties of reactive powder or liquid samples, allowing the measurement of various electrical parameters to be carried out. The present invention provides the chamber in two variants of embodiment: the multiple use chamber and the single use chamber. The construction of the chamber provides the possibility of carrying out the measurements with the sample placed directly between parallel active surfaces of the electrodes placed coaxially and sliding in a precise manner in to a thin-walled cylinder made of insulating material providing electric insulation. Elements remaining in contact with the sample are made of chemically inert materials. Additionally, a module containing a pair of
(Continued)

the electrodes and the cylinder made of insulating material is detachable from the rest of device elements, that enables its loading and hermetic closure in a glovebox filled with inert gas. The device provides the possibility of carrying out the electrochemical measurements as a function of temperature and pressure. The present invention also refers to a method of carrying out measurements of electrical properties of reactive powder or fluid samples, wherein a sample is loaded into a measurement chamber in an inert gas atmosphere, then the gaseous phase is removed from spaces between parallel active surfaces of electrodes and additionally, solid samples are subjected to compression, and then in the system of regulated temperature and/or pressure a measurement of a selected electrical parameter as a function of time and/or temperature and/or pressure is carried out.

24 Claims, 13 Drawing Sheets

(58) Field of Classification Search
CPC ...... G01N 31/16; G01N 27/417; G01R 11/04; G01R 27/22; G01R 33/305; G01R 33/31; B01F 15/00227
See application file for complete search history.

(56) References Cited

U.S. PATENT DOCUMENTS

| | | | |
|---|---|---|---|
| 4,160,714 A * | 7/1979 | Andersen | ............ G01N 27/403 204/411 |
| 5,140,273 A | 8/1992 | Takahashi | |
| 5,280,429 A | 1/1994 | Withers | |
| 5,451,882 A | 9/1995 | Wakino | |
| 6,413,255 B1 * | 7/2002 | Stern | ............ A61B 18/14 606/41 |
| 7,443,175 B2 * | 10/2008 | Podhajsky | ............ G01N 27/221 324/663 |
| 2008/0030206 A1 | 2/2008 | Podhajsky | |
| 2009/0039900 A1 | 2/2009 | Podhajsky | |

OTHER PUBLICATIONS

Badwal SPS, Solid State Ionics, 76 (1995), p. 67-80.
Bredikhin S, Solid State Ionics, 136-137 (2000), p. 387-392.
Hjelm AK et al, Electrochimica Acta, 48 (2002), p. 171-179.
Bohn HG et al, Solid State Ionics, 117 (1999), p. 219-228.
Schonau K et al, Journal of Applied Physics, 92 (2002), p. 7415.
Fontanella JJ et al, Journal of Applied Physics, 60 (1986), p. 2665-2671.
Fontanella JJ et al, Macromolecules, 29 (1996), p. 4944-4951.
Edmondson CA et al, Solid State Ionics, 85 (1996), p. 173-179.
Lisovytskiy D et al, Solid State Ionics, 176 (2005), p. 2059-2064.
Fijalkowski K et al, Physical Chemistry Chemical Physics, 14 (2012), p. 5778-5784.
Malinowski PJ, Derzsi M, Jurczakowski R, Mazej Z, Grochala W, submitted 2013.

* cited by examiner

CELL AND METHOD FOR ELECTRICAL MEASUREMENTS OF HIGHLY REACTIVE POWDER AND LIQUID SAMPLES

A chamber for measurements of electrical properties of highly reactive powder or liquid samples and a method of carrying out measurements of the electrical properties of highly reactive powder or liquid samples An invention refers to the chamber for the measurements of the electrical properties of the powder or liquid samples, allowing carrying out the measurements of various electrical parameters (an electrical impedance, an admittance, a dielectric constant) and to the method of carrying out the measurements of the electrical properties of the powder or liquid samples in a function of a frequency of electric field, temperature, pressure and time changes.

An impedance spectroscopy is a technique that is widespread and routinely used for the measurements of the electrical properties of solids. An impedance spectroscopy is based on the interaction of a matter with an alternating electric field, resulting from a the movement of stable or induced electric dipoles and charge carriers. The dipole relaxation in alternating electric field depends on the temperature and a local viscosity of a medium, resulting from a chemical surrounding of the dipoles and external pressure. An electrical equivalent circuit describing the impedance of a physicochemical system can be treated as a combination of elements, which accumulate and/or dissipate energy, wherein using appropriate data interpretation, it is possible to obtain with this method structural information for various materials. Currently, this method finds applications in studies of colloidal systems, polymer systems, and recently also systems of a pharmaceutical and biological importance, to name a few (U.S. Pat. No. 5,280,429). As a result of a recent technological progress new materials having unique properties are formed, being often characterised by high chemical reactivity and/or thermodynamic instability, so that they cannot be exposed to ambient conditions—a moisture and oxygen from the air. Additionally, these later factors often affect to a large extent the dielectric properties even during the measurements of the thermodynamically stable substances.

Currently, the impedance measurements are carried out routinely by using a solution similar to that described in American U.S. Pat. No. 5,140,273. The measurements are carried out for the samples in the form of hard pastille, which is coated by a thin layer of a noble metal, in order to provide an appropriate electrical contact, which are subsequently connected to the electrodes of the impedance spectrometer. For providing an electrical contact, binders, lacquers and conducting liquids of various kinds are also used, however these later are characterised by a low chemical resistance and they can not be used for providing the electrical contacts for the reactive samples (S. P. S. Badwal, *Solid State Ionics,* 76 (1995) 67-80). Additionally, all operations described above are carried out in the presence of atmospheric oxygen and moisture, what makes impossible to test the reactive chemical compounds that are sensitive for these factors. Necessity of previous pelletising of the powder samples also often generates problems. The powdery samples that are poorly pressed have usually very large resistance at grain boundaries.

In the state of the art there are known methods of carrying out the measurements of the impedance spectroscopy in high temperatures. This aim is achieved by different methods depending on the required temperature range. Moderately high temperatures are obtained by heating the examined sample by using thermostat (S. Bredikhin, *Solid State Ionics,* 136-137 (2000) 387-392; A. K. Hjelm et al., *Electrochimica Acta,* 48 (2002) 171-179), immersing hermetically packed sample with the electrical contact placed into the container with thermostated liquid. Very high temperatures are obtained by using ovens (H. G. Bohn et al., *Solid State Ionics,* 117 (1999) 219-228) in which the examined sample can be placed with electrical contact. Low temperatures are obtained by means of special cryostats (K. Schonau et al., *Journal of Applied Physics,* 92 (2002) 7415). In all cases the temperature is obtained very precisely, however it needs to use additional laboratory equipment.

Until now, it was possible to carry out the impedance measurements under increased pressure by using pressure vessels (see e.g.: J. J. Fontanella, et al, *Journal of Applied Physics,* 60 (1986) 2665-2671; J. J. Fontanella et al., *Macromolecules,* 29 (1996) 4944-4951; C. A. Edmondson et al., *Solid State Ionics* 85 (1996) 173-179). The pressure vessel is filled with liquid medium (e.g. Spinesstic 22—a lubricant, crude oil fraction), wherein a leak proof rubber container containing the examined sample is immersed. The pressure is applied mechanically from the outside into the vessel and is transferred hydraulically on the sample by using this medium. It allows slow and precise obtaining of uniform pressure in the narrow range usually not exceeding 0.5 GPa (5000 atmospheres). This method is expensive and labour-consuming, and its application in the laboratory in order to achieve the pressures exceeding 1 GPa, needs to use additional very complicated and expensive apparatus.

In the state of the art there is known a measurement system containing transparent electrodes (see e.g.: D. Lisovytskiy et al., *Solid State Ionics,* 176 (2005) 2059-2064). Such solution allows carrying out optical measurements (a microscope with polarized light) and X-ray diffraction measurements during the measurements of the electrical properties. It allows for monitoring of a current state of the samples at every stage of the measurement.

There is known an invention according to American U.S. Pat. No. 5,140,273 enabling carrying out the measurements of the impedance spectroscopy for the powder samples without an initial step of pelletising of the powdery sample. Tested powder is placed between two electrodes with parallel surfaces, which are movable coaxially inside a stabilising channel. The lower electrode is placed in a fixed manner inside the device, and after pouring the powder the upper electrode is placed coaxially inside the stabilising channel and is tighten up. The electrodes and the stabilising channel are integral parts of the spectrometer, what makes impossible to load the samples and tighten the apparatus in the inner atmosphere. The necessity of carrying out the loading operations of the samples outside a glove box filled with inner gas makes impossible to test the samples which are sensitive to contact with oxygen and atmospheric moisture.

The invention according to American U.S. Pat. No. 5,451,882 allows for carrying out the measurements of dielectric constant of powder samples, which are dispersed in a fluid phase of a known dielectric constant. The examined sample is introduced between two electrodes which are placed coaxially, slidingly and strictly in a cylinder with thick-walled insulating material, providing an electric insulation. The insulating material is thick enough to provide stiffness of the electrode system. The electrodes are placed at a fixed distance in the range from 4.5 to 5.5 mm, without theirs compression under increased pressure. The fixed and well defined distance between these electrodes is very important for accuracy of the measurements. However, the solution according to U.S. Pat. No. 5,451,882 does not allow for carrying out the measurements of dried powder samples, because it does not provide sufficiently strong clamp of the electrodes for appropriate compression of the tested powder. Insufficient compression of the tested powder considerably reduces its conductivity, what affects obtained results.

A device according to China utility model CN2141899Y provides possibility of carrying out measurements of electrical resistance of powder samples in a function of applied pressure. The examined powdery sample is placed between two cylindrical electrodes, which are placed coaxially and sliding in to a cylinder made of insulating material surrounded by a stabilising ring that assures the stiffness of an electrode system. The electrodes are clamped by using an integrated press, wherein an operative force is transferred by means of a screw. The thickness of the tested sample arranged between the electrodes is measured by means of a micrometer screw. However, a solution according to China utility model CN2141899Y does not allow for testing the samples, which are chemically reactive, because a module containing the electrodes does not maintain the leak tightness relative to atmospheric air. Due to a fixed mounting of the electrodes in the measurement device it is not possible to detach the module containing the electrodes and to load it inside the glove box. This device also does not allow for carrying out the measurements in a function of temperature nor allows to direct observation of the samples during conducting of the measurement.

A device according to China utility model CN2135157 constructional is very close to the device according to CN2141899Y: an examined powdery sample is placed between two cylindrical electrodes, which are placed coaxially and sliding in to a cylinder made of the insulating material surrounded by a stabilising ring that assures the stiffness of the electrode system, the electrodes are clamped by using an integrated press, wherein an operative force is transferred by means of a screw, and the thickness of a layer of the tested sample arranged between the electrodes is measured by means of a micrometer screw, an electrodes are similarly seated in an installation transferring the pressure.

Thus, there is a long realised and unsatisfied need for a solution that allows for carrying out studies of the electrical properties of the reactive powder samples in a function of time, frequency of an electric field changes, pressure and/or temperature. Known measurement devices are not adapted to carry out the measurements for the high reactive samples, are not made of materials of high chemical resistance nor do not contain a detachable measurement module, which could be easily detached from the whole device and filled up with the sample in a glove box in an inert gas atmosphere. Additionally, the measurement chambers known from the prior art for carrying out the measurements of the electrical properties are characterised by high degree of the construction complexity and high cost of the production.

The solution according to the present invention, in particular the presented variants of the chamber for measurements of the electrical properties of reactive powder or liquid samples and the method of carrying out the measurements of the electrical properties of reactive powder or liquid samples, solve the problems and drawbacks known from the state of the art.

A multiple use chamber for the measurement of the electrical properties of powder or liquid samples, comprising a measuring module comprising two cylindrical electrodes with stabilising flanges coaxially arranged and sliding in to a cylinder made of insulating material providing electric insulation, surrounded by a stiffening ring, in which chamber the electrodes are compressed using a clamping system generating high pressure, equipped with a pressure measurement system, with an examined sample being placed between parallel active surfaces of the electrodes, according to the present invention is characterised in that the measuring module constructed from the electrodes placed in the cylinder made of insulating material and surrounded by the stiffening ring is placed detachably in the clamping system generating high pressure, wherein the electrodes are placed in the cylinder made of insulating material in a precise manner assuring air tightness of the measurement system.

Preferably, in the multiple use chamber according to the present invention the electrodes are made of chemically inert material with a high hardness and having a good electric conduction, preferably such as hardened steel, monel, titanium, tungsten, tungsten carbide or titanium-molybdenum alloy.

Preferably, in the multiple use chamber according to the present invention an active surface of the electrodes is coated with a thin layer of chemically inert compound, preferably with an electrode metal oxide, polytetrafluoroethylene (PTFE) or a diamond doped with boron (BDD), or alternatively is coated with the layer of the chemically inert metal.

Preferably, in the multiple use chamber according to the present invention in the middle part of the stiffening ring, in a region of contact of the active surfaces of the electrodes with a sample, the chamber has an inspection opening, and a cylinder made of insulating material is made of transparent material, preferably polytetrafluoroethylene (PTFE) or perfluorinated ethylene/propylene copolymer (FEP).

Alternatively, in the multiple use chamber according to the present invention the inspection opening is formed by at least one horizontal recess in the stiffening ring, not exceeding ⅔ of a circumference of the stiffening ring.

According to the invention, the multiple use chamber according to the present invention further comprises around the stiffening ring a temperature stabilising and regulating system is arranged, preferably in the form of an electric heater, a thermostated fluid tank, a thermostated chamber, an oven or a coil pipe multiply surrounding the stiffening ring, wherein the coil pipe is preferably mounted on a metal sleeve preferably made of silver.

According to the invention, the multiple use chamber according to the present invention it further comprises stabilising covers for compression in a press, wherein a surface of the stabilising cover remaining in contact with the stabilising flange of the electrode has a seat of a shape and size corresponding to the shape and size of the stabilising flange of the electrode, wherein in walls surrounding the seat in a surface of the stabilising cover, a recess allowing for a placement in the seat of an electrical contact preferably in the form of a flat plate is arranged, and the surface of the stabilising cover opposite to the surface with the seat is covered by a layer of an electrical insulator.

According to the invention, the multiple use chamber according to the present invention further comprises a clamping installation, containing compression plates connected with each other by means of screws, and the surface of the compression plates directed towards the flange of the electrode is covered by the layer of an electrical insulator, wherein between the stabilising flange of the electrode and the layer of the electrical insulator the electrical contact, preferably in the form of the flat plate, is arranged.

According to the invention, the multiple use chamber according to the present invention further comprises a clamping installation for automatic pressure regulation, containing three compression plates with parallel surfaces mounted on rigid guides, wherein two terminal covers are permanently connected with the guides, and the middle cover can be moved along the guides, wherein this installation is provided with a hydraulic actuator that is electronically controlled and coupled with an electronic pressure measurement system, and the surface of the compression plates directed towards the flange of the electrode is covered by the layer of an electrical insulator, wherein between stabilising flange of the electrode and the layer of an electrical insulator, the electrical contact, preferably in the form of the flat plate, is arranged.

Preferably, in the multiple use chamber according to the present invention the electrode has rounded edges of the active surface of the electrode.

A single use chamber for measurements of the electrical properties of powder or liquid samples, comprising a measuring module comprising two cylindrical electrodes coaxially arranged and sliding in to a cylinder made of insulating material providing electric insulation, surrounded by a stiffening ring, the chamber comprising an examined sample between active surfaces of the electrodes, according to the present invention is characterised in that the electrodes take the form of cylinders with parallel active surfaces directed into the interior of the chamber, mounted inside a thin-walled cylinder made of insulating material, surrounded by a thin-walled stiffening ring, wherein the sum of the lengths of the electrodes exceeds by 5-30% the length of the cylinder and the length of the stabilising ring, and the length of the cylinder is larger than the length of the stabilising ring, also in that the active surface of the electrodes and the cylinder are made of chemically inert materials.

Preferably, in the single use chamber according to the present invention the cylinder made of insulating material is constructed from polytetrafluoroethylene (PTFE) or perfluorinated ethylene/propylene copolymer (FEP).

Alternatively, in the single use chamber according to the present invention the electrodes and the stiffening ring are made of soft metal alloy, preferably acid resistant steel or titanium.

Preferably, in the single use chamber according to the present invention the active surface of the electrode is coated with a thin layer of chemically inert compound, preferably with the metal oxide of the electrode, polytetrafluroethylene (PTFE) or diamond doped with boron (BDD) or alternatively is coated with a layer of a specified metal.

According to the invention, the single use chamber according to the present invention further comprises disposable detachable flexible stabilising holder and a system for compressing the chamber filled with a sample and enclosed by the electrodes, having the form of a thick-walled metal cylinder, with a blanking plug and a cylindrical piston which are placed coaxially and slide in to the cylinder in a precise manner assuring air tightness, and the system for compressing is made of metal alloy with a high hardness.

According to the invention, the single use chamber according to the present invention further comprises a two-piece, hermetic housing containing electrical contacts and is provided with a temperature stabilising and regulating installation, preferably in the form of an electric heater, a thermostated fluid tank, a thermostated chamber, an oven or a coil pipe, multiply surrounding the hermetic housing.

Preferably, in the single use chamber according to the present invention the electrode has rounded edges.

The present invention also refers to a method of carrying out measurements of the electrical properties of powder or fluid samples, which according to the invention is characterised in that the reactive sample is loaded into the measurement chamber defined in claim 1 or 11 in an inert gas atmosphere, gaseous phase is removed from the space between the parallel active surfaces of the electrodes and additionally, solid samples are subjected to compression, and then in the system of a regulated temperature and/or pressure, the measurement of a selected electrical parameter as a function of time and/or frequency of electric field changes, and/or temperature, and/or pressure is carried out.

Preferably, in the method according to the present invention the measurement of the solid sample thickness is carried out after the measurement of the electrical parameter is completed and after the opening of the measurement chamber in an inert gas atmosphere or the thickness of the sample is determined from a difference between geometric parameters of empty and loaded chamber.

Preferably, in the method according to the present invention the thickness of the fluid sample is determined from the difference between geometric parameters of empty and loaded chamber or is calculated based on the known volume of tested liquid and a diameter of the chamber.

Preferably, in the method according to the present invention during the measurement of the electrical parameter an inspection opening is used for monitoring the current state of the sample subjected to the measurements of the electrical properties by using spectral measurements, X-ray diffraction, optical techniques or a visual observation.

The solution according to the present invention allows one to carry out the measurements for the samples, which are chemically reactive, and are in the form of powders and liquids, is obtained. The powdery samples are placed directly between the electrodes in the chamber and pressed just directly between the electrodes, what provides possibility of carrying out the measurements without initial step of pelletising outside the testing apparatus. It is also possible to test routinely the fluid samples. Innovative construction gives a possibility of carrying out the measurements of the neat samples, without addition of any substances assuring the electrical contact, such as binders, lacquers and metal layers deposited by sputtering, is obtained. Thanks to the application in the construction chemically inert materials, it is possible to carry out the measurements of highly reactive samples. Small size of the chamber makes it very mobile, and easy to be filled up without any problems in the glovebox filled with an inert gas, and then after hermetic closure the chamber can be subjected further operations, which allows carrying out the measurements de facto in the inert gas atmosphere. It provides a possibility of testing the reactive samples and sensitive to contact with oxygen and the atmospheric moisture. The chamber according to the present invention is presented in the variant enabling multiple use of device and in the variant for single use only.

Additionally in the variant of the chamber for multiple use, thanks to the application of an additional inspection opening, the possibility of monitoring of a current state of the samples during its compression and of carrying out measurements of the electrical parameters is obtained. The monitoring of the sample state can be carried out by using the spectral measurements, X-ray diffraction, optical techniques or visual observation conducted in a real-time in situ, inside the chamber during carrying out measurements of the electrical parameter. Thanks to the application of additional covers and holders, it is possible to carry out of the measurements of the electrical properties in a function of applied pressure, allowing for elimination of the effects resulting from insufficient compression of the powder samples and carrying out the measurements for high-pressure polymorphic modifications. Thanks to the application of the stabilising temperature system, it is possible to carry out of the measurements in the function of the temperature. Thanks to the application of the innovative construction of the chamber, after completion of the measurements of the electrical properties it is possible to carry out of further tests of the samples for monitoring of the structural and spectral changes produced by the applied pressure and temperature.

Additionally, in the variant of the single use chamber, thanks to the very small size of the chamber, it is possible to test the samples in a micro-scale; the weighted sample does not exceed 2 mg.

The chamber according to the present invention is described below with reference to accompanied drawings, wherein:

FIG. 1 illustrates the chamber according to the present invention in the variant for multiple use in a vertical section along a diameter of the cylindrical electrodes, FIG. 2 illustrates the chamber according to the present invention in the variant for multiple use in a side view, FIG. 3 illustrates the chamber according to the present invention in the variant for multiple use equipped with temperature stabilising and regulating installation in the form of coil pipe, in the vertical section along the diameter of the cylindrical electrodes, FIG. 4 illustrates the chamber according to the present invention in the variant for multiple use equipped with temperature stabilising and regulating installation in the form of coil pipe, in the side view, FIG. 5 illustrates the chamber in the variant for multiple use placed in stabilising covers in the vertical section along the diameter of the cylindrical electrodes, the cross-section through the stabilising covers was directed through the recess enabling the connection to the electrical contact, FIG. 6 illustrates the chamber according to the present invention in the variant for multiple use placed in the stabilising covers in the side view.

FIG. 7 illustrates the chamber according to the present invention in the variant for multiple use placed in the stabilising covers in the press, in the side view with marked pistons of the press and direction of the clamp, in the vertical section along the diameter of the electrodes, FIG. 8 illustrates the stabilising cover for the chamber according to the present invention in the variant for multiple use in a view from the side of the electrodes, FIG. 9 illustrates the chamber according to the present invention in the variant for multiple use placed in the compression system with the screws, in the vertical section along the diameter of the cylindrical electrodes, FIG. 10 illustrates the chamber according to the present invention in the variant for multiple use placed in the compression system with the screws, in the side view, FIG. 11 illustrates the chamber according to the present invention in the variant for multiple use placed in the compression system with a hydraulic actuator, in the vertical section along the diameter of the cylindrical electrodes, FIG. 12 illustrates the chamber according to the present invention in the variant for multiple use placed in the compression system with the hydraulic actuator, in the side view, FIG. 13 illustrates the cylindrical electrode of the chamber in the variant for multiple use with rounded edges of the active surface and a stabilising flange, in the vertical section along the diameter of the electrode; the rounded edge is also presented in a magnification, FIG. 14 illustrates the chamber according to the present invention in the variant for single use only in the vertical section along the diameter of the cylindrical electrodes, FIG. 15 illustrates the chamber according to the present invention in the variant for single use only in the side view, FIG. 16 illustrates a flexible stabilising holder for compression of the chamber according to the present invention in the variant for single use only in the press, in a top view, FIG. 17 illustrates the chamber according to the present invention in the variant for single use only in the stabilising holder during compression, placed in the compression system with marked pistons of the press and the direction the clamp, in the vertical section along the diameter of the electrodes, FIG. 18 illustrates the chamber according to the present invention in the variant for single use only after completion of the compression, in the vertical section along the diameter of the cylindrical electrodes, FIG. 19 illustrates the chamber according to the present invention in the variant for single use only after completion of the compression, in the side view, FIG. 20 illustrates the chamber according to the present invention in the variant for single use only equipped with a two-piece hermetic housing in the side view, FIG. 21 illustrates cylindrical electrode of the chamber in the variant for single use only with rounded all edges, in the vertical section along the diameter of the electrode; the rounded edge is also presented in the magnification.

DETAILED DESCRIPTION OF THE INVENTION AND THE DRAWINGS

As mentioned above, from a long time on the market there has been unsatisfied need for the solution enabling carrying out the measurements of the electrical properties of the reactive powder samples in the function of the frequency of the electric field, the temperature, the pressure and the time changes. The measurements of the electrical properties of the powder samples are routinely commonly carried out, but a measurement procedure is not adapted for testing of the reactive samples. Particularly dangerous for the reactive samples are steps of the measurement procedure that are carried out in the atmospheric air containing oxygen and moisture reacting with the samples of a material. It is about the step of pelletising of the powdery sample, the step of the deposition of the thin layer of the electrical contact by sputtering on the pellet and the step of the measurement carried out in the spectrometer.

The step of pelletising alone is a key step for the correct carrying out the measurement, because the compression of the powder in an insufficient way results in appearance of an additional resistance at the boundary of the grains, what falsifies the real value of the conductivity of the tested sample. So far, the degree of the compression of the samples could be determined only after deposition of the electrical contact by sputtering on the obtained pellet and carrying out the first measurement. According to the prior art, in the case of insufficient compression of the powder the obtained pellet becomes useless and it should be prepared a new pellet with deposition on this pellet the electrical contact by sputtering.

In the state of the art it was also possible to carry out the measurements in the function of the temperature and the pressure. However, desired temperature is obtained inside the measurement chamber of the spectrometer, which is inconvenient because of a long time of the temperature stabilisation.

The high pressures—in the state of the art, are obtained by using special systems containing the measuring module and a power press. However, these devices are not adapted to the contact with the reactive chemical compounds.

In the state of the art are not known devices allowing for simultaneous carrying out the measurements in the function of the pressure and the temperature. Additionally, the measurement chambers known from the prior art for carrying out the measurements of the electrical properties are characterised by high degree of the construction complexity and high cost of the production.

Figure 1:
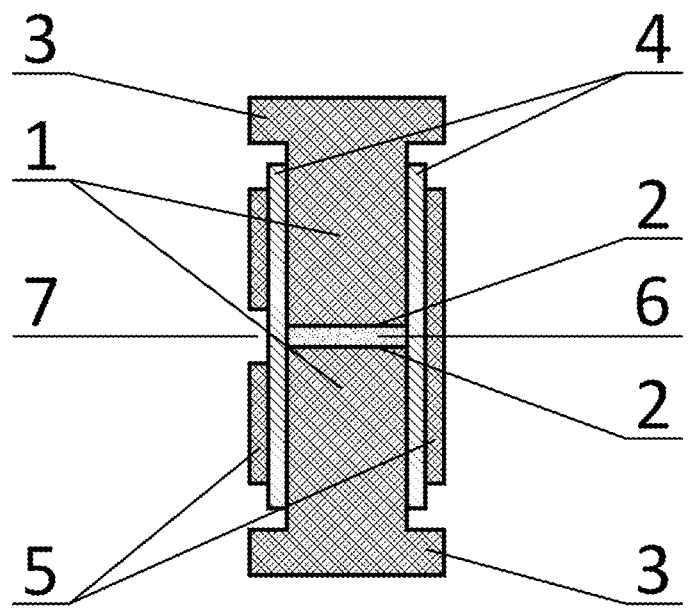
Figure 2:
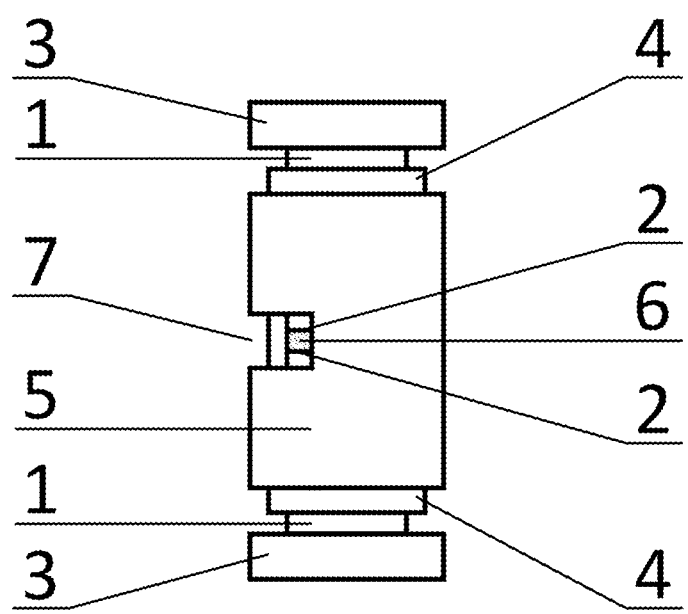

The chamber according to the present invention in the variant for multiple use, illustrated on the FIG. 1 and FIG. 2, allows for omission of the steps of pelletising and deposition of the electrical contact on the pellet by sputtering. According to the invention, the reactive powdery sample is placed directly between the electrodes serving as a structural component of the chamber according to the present invention. It allows for currently monitoring of the compression degree of the samples and possible increase of the pressure in order to obtain better compression and elimination of the resistance at the boundary of the grains.

Small size of the chamber according to the present invention make possible its filling up and the hermetic closure inside the glove box filled with inert gas, which provides a lack of the contact with oxygen and atmospheric moisture. After closure of the chamber, the sample is pressed directly between the electrodes inside or outside the glove box. The step of the measurement is carried out de facto in the inner atmosphere, thanks to the hermetic closure of the chamber according to the present invention. Thanks to the application of the chemically inert materials in the construction of the chamber according to the present invention, the risk of damage of the reactive samples considerably decreases, and in the most of cases is practically eliminated. Thanks to the application of stable, chemically inert construction materials, the chamber A according to the present invention can be multiply used.

The use of the chamber according to the present invention in the variant for multiple use allows significantly to reduce the costs of the carried out measurements of the electrical properties due to the elimination of the step of the deposition of the electrical contact on the tableted powdery sample by sputtering, carried out in expensive sputter coaters. Simultaneously, the construction of the chamber according to the present invention is very simple and has small sizes, which reduce the costs of their production, thus additionally reduce the costs of carrying out the measurements of the electrical properties of solid powder samples.

Thanks to the application of the special inspection opening in the chamber according to the present invention in the variant for multiple use, it is possible to monitor the current state of the samples at every stage of the measurement procedure by using the spectral measurements, X-ray diffraction, optical techniques or visual observation. Thanks to the simple construction and elimination of the step of deposition of the electrical contact by sputtering, the chamber according to the present invention allows for non-invasive carrying out the measurements of the electrical properties and gives a possibility of the further testing of the powdery samples by the other methods after completion of the electrical measurement and re-opening of the chamber.

In the FIG. 1, the chamber is presented in the vertical section along the diameter of the electrodes 1 whereas in the FIG. 2—in the side view. The multiple use chamber has two cylindrical electrodes 1 coaxially arranged slidingly and strictly in a thin-walled cylinder 4 made of the insulating material providing an electric insulation, surrounded by a stiffening ring 5. The electrodes 1 take a form of cylinders with an active surface 2 directed towards an interior of the chamber A and an additional stabilising flange 3 at the opposite end. Between the active surfaces 2 of the electrodes 1 the sample 6 is arranged. In the middle part of the stiffening ring 5 in a region of a contact of the active surfaces 2 of the electrodes 1 with the sample 6 an inspection opening 7 is arranged. The inspection opening 7 is formed by at least one horizontal recess in the stiffening ring 5, not exceeding ⅔ of a circumference of the stiffening ring 5.

The electrodes 1 are made of hard material with a high hardness, and having a good electric conduction, preferably hardened steel, monel, titanium, tungsten, tungsten carbide or titanium-molybdenum alloy. In the case of carrying out the measurements of the reactive samples, the material of the electrode must be chemically inert so as to not react with the tested reactive sample 6, which the electrodes 1 have direct contact with. The application of hard metals allows compression of the powder samples under high pressure greater than 2 GPa (20000 atmospheres) without deformation of the electrodes 1, thus without the damage of the chamber. So high pressure can be obtained by using common laboratory pelleting machine, which is routinely used for preparation of KBr pellets for the spectral measurements in infrared (a load up to 15 tons). When the diameter of the electrode 1 is 1 cm, surface area of the electrode is 0.785 $cm^2$, which means that by applying the load of 15 tons, the pressure of 1.91 GPa is obtained. Constructing the chamber according to the present invention and using electrodes of the diameter in the range from 0.4 cm to 2 cm, the pressure of pelletising from 0.4 GPa even up to 3.0 GPa for the electrodes of the smallest diameter can be obtained. The application of the electrodes of a smaller diameter carries a risk of instability of the chamber during compression, which can lead to failure to maintain a parallelism of the active surfaces 2.

The electrodes 1 can be moved slidingly and coaxially inside the thin-walled cylinder 4 made of the insulating material, providing an electric insulation. The application of the cylinder 4 is a necessary condition for hermetic closure of an examined sample 6 inside the chamber according to the present invention. The cylinder 4 must be an electrical insulator so as not to lead to a short circuit of the electrodes 1. In the case of carrying out the measurements of the reactive samples, the cylinder 4 must be made of the chemically inert material so as to stay neutral in relation to the reactive powder samples, which have direct contact with. to provide a possibility of taking advantage of the inspection opening 2, this material must also be transparent. Alternatively, the cylinder 4 can be made of ceramic material.

The cylinder 4 is arranged inside of the stiffening ring 5 which provides a stiffness to the chamber during compression. A maintaining of the stiffness of the system allows keeping a coaxiality of the electrodes 1 and the parallelism of their active surfaces 2 between which the examined sample 6 is pressed. The cylinder 4 is longer that the stiffening ring 5 by 5-20%, it eliminates the risk of the short circuit of the electrodes 1 during carrying out the measurement.

The inspection opening 7 is arranged in the side wall in the middle part of the stiffening ring 5 in the region of the contact of the active surfaces 2 of the electrodes 1 with the sample 6. It allows at every stage of the measurement procedure for currently monitoring of a state of the tested sample 6 by using an optical, visual and spectral methods. The inspection opening 7 is formed by the horizontal recess in the material of the stabilising ring 5 not exceeding ⅖ of its circumference. The application of the inspection opening 7 of greater sizes would reduce the stiffness of the stiffening ring 5 which would lead to its deformation during the compression step. The inspection opening 7 can take a form of one wide recess, and then the measurements by using optic techniques and the visual observation is much simpler and there can be conveniently applied reflection spectral techniques. The application of the inspection opening 7 in the form of pair of the openings allows for the monitoring of the sample state 6 by using the spectroscopic measurements and diffraction measurements with a beam passing through the sample.

The electrodes 1 are equipped with the stabilising flanges 3. Thanks to such construction, the chamber is stable during the step of pelletising and it is easier to keep the parallelism of the active surfaces 2 of the electrodes 1 during carrying out the measurement.

The measurement of the tested layer thickness of the powdery sample 6 pressed between the active surfaces 2 of the electrodes 1 is carried out after completion of the measurement and opening the chamber. The measurement of the thickness of the sample layer 6 is carried out using a precise measurement tool, for example the slide caliper. The chamber is opened very easy by withdrawing the electrodes 1 from its inside. The shape of the electrodes 1 equipped with the stabilising flanges 3 significantly facilitates the process of withdrawing of the electrodes from inside of the chamber. Alternatively, the thickness of the layer of the tested sample 6 is determined from the difference between the geometric parameters of the empty and the loaded chamber. The height of the empty chamber and the chamber containing the sample 6 is measured and the difference of the heights is equal to the thickness of the sample 6. Alternatively, in the case of carrying out the measurements of the fluid samples, the thickness of the layer of the tested sample 6 is calculated based on known volume of tested liquid and the diameter of the chamber.

Figure 3:
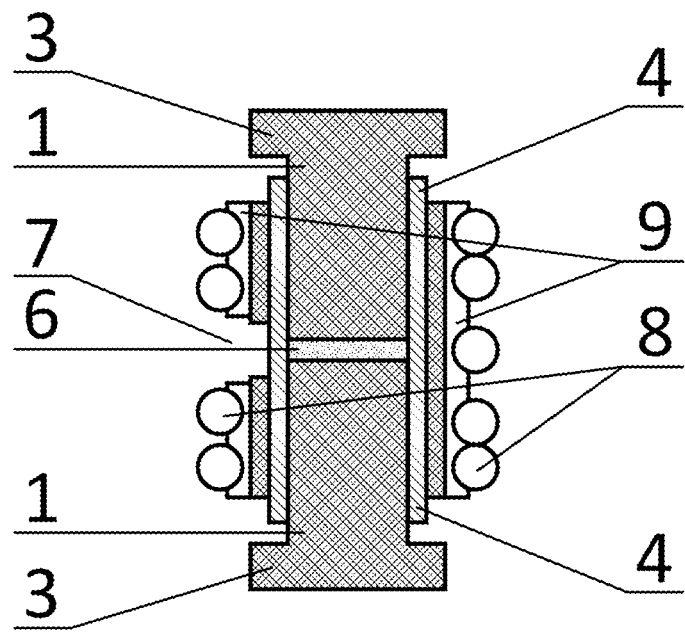
Figure 4:
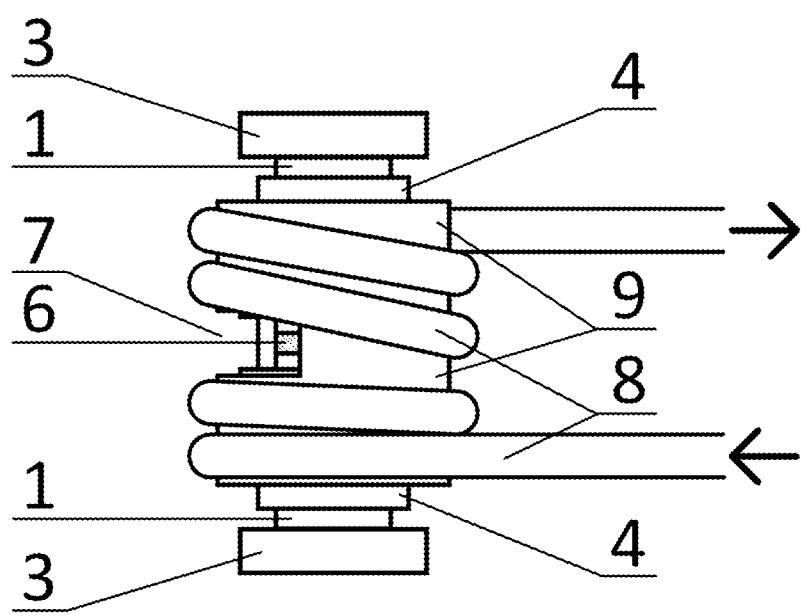

As mentioned before, the chamber according to the present invention in the variant for multiple use allows also for carrying out the measurements of the electrical properties by using additional temperature stabilising and regulating system presented in the FIG. 3 and FIG. 4. According to the invention it is possible to stabilise and regulate the temperature and its control on the outside wall of the chamber by using a thermocouple or a thermometer.

In the FIG. 3, the chamber surrounded by the temperature stabilising and regulating system 8 is presented in the vertical section along the diameter of the electrodes 1, whereas in the FIG. 4—in the side view. The chamber further comprises the temperature stabilising and regulating installation placed around the stiffening ring 5. The temperature stabilising and regulating system has a form of coil pipe 8 seated in a fixed manner on a metal sleeve 9 and multiply surrounding it. The sleeve 9 preferably made of silver has a size matching the size of the stiffening ring 5, connected with the outside thermostat so that through the coil pipe a medium of a desired temperature is flowed.

The temperature stabilising and regulating installation 8 allows for carrying out the measurements of the electrical properties in the function of temperature, what is extremely important for determination of the electrical parameters, such as activation energy. The installation 8 can take a form of an electric heater or the coil pipe multiply surrounding the stiffening ring 5 of the chamber, connected with the outside thermostat. In the variant utilizing the coil pipe, it is connected with the outside thermostat. Depending on the used medium, the temperature in very wide range can be obtained, depending only on the used medium, e.g. the use of ethylene glycol allows to obtain the temperature in the range from −30° C. to +190° C., and the use of diethyl ether gives the range of temperatures from −110° C. to +25° C.

The control of the current temperature of the chamber can be carried out by using the thermocouple or the thermometer that is placed on the outside wall of the stiffening ring 5. The temperature may also be determined based on the measurement of the temperature of the medium stream leaving the thermostat and the recycle stream. This entails a certain degree of uncertainty of a result, but allows reducing the costs of the carried out measurements.

As mentioned above, the chamber according to the present invention, in the variant for multiple use, allows for carrying out the measurements in the function of the applied pressure by using the additional stabilising covers presented in the FIGS. 5-12. According to the invention, it is possible to control of the amount of the pressure applied on the examined powdery sample and to control of the degree of its compression. It is also possible to carry out of the measurement of the electrical properties in the function of the applied pressure. Value of the applied pressure can be calculated knowing the amount of pressure and the surface area of the electrodes or using an additional pressure measurement system.

Figure 5:
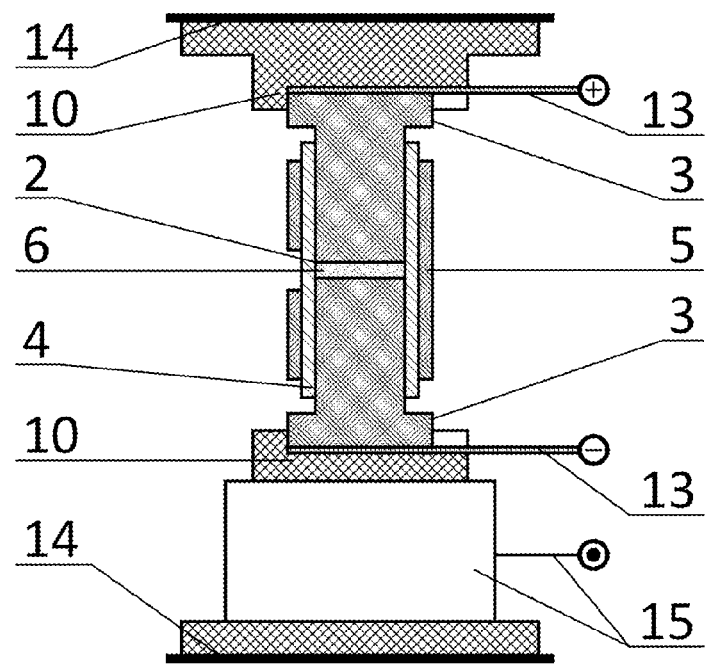
Figure 6:
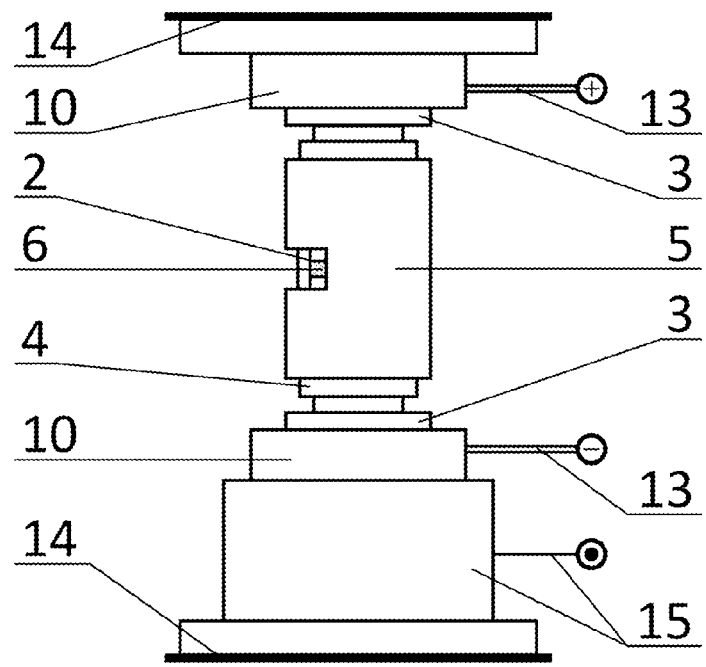
Figure 7:
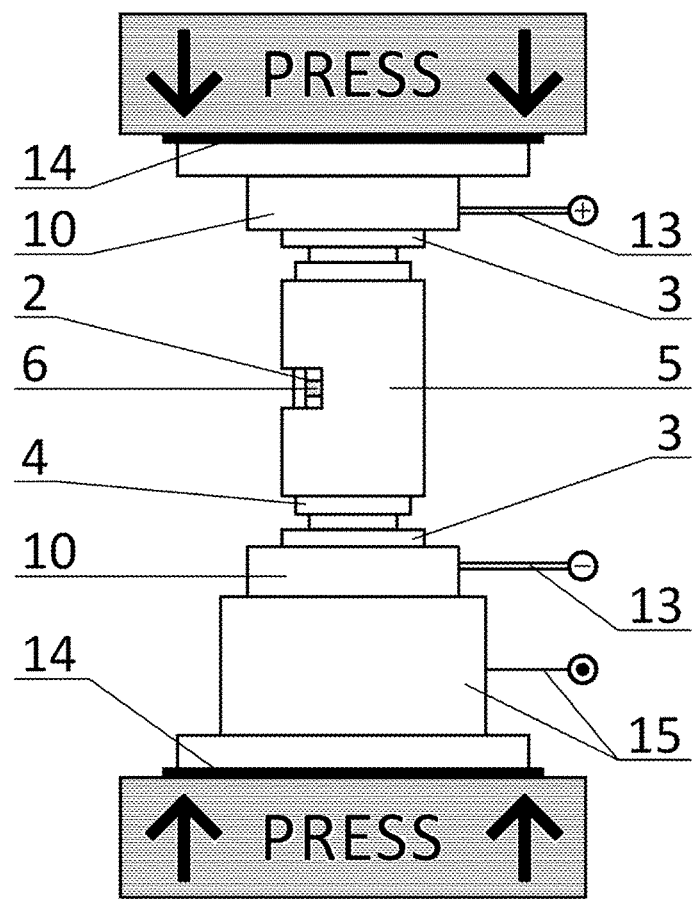

In the FIG. 5 the chamber in the stabilising covers 10 is presented in the vertical section along the diameter of the electrodes 1 and in the FIG. 6 in the side view, whereas in the FIG. 7 in the side view with indication of the direction of the pressure of the press pistons. The chamber further comprises the stabilising covers 10 for compression in the press, and the surface of the stabilising cover 10 remaining in the contact with the stabilising flange 3 of the electrode 1 has the seat 11 of a shape and size corresponding to the shape and size of the stabilising flange 3 of the electrode 1. In walls surrounding the seat 11 in the surface of the stabilising cover 10 is arranged the recess 12 allowing for a placement in the seat 11 of the electrical contact 13 preferably in the form of a flat plate. The surface of the stabilising cover 10 opposite to the surface with the seat 11 is covered by the layer of an electrical insulator 14. Between the stabilising covers 10 and the stabilising flange 3 of the electrode 1, a system 15 for the measurements of the of the pressure applied on the sample is arranged, preferably based on the application of a piezoelectric element.

Figure 8:
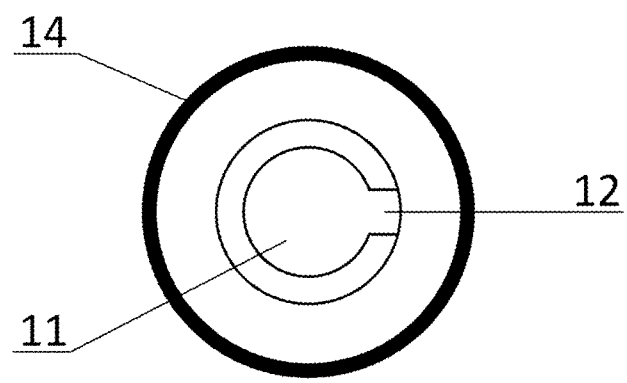

In the FIG. 8 the stabilising cover 10 of the chamber is presented in the view from the side directed towards the electrode and shows a position of the seat 11 of the recess 12 allowing for housing in the seat 11 of the electrical contact 13 and layers of the electrical insulator 14.

The stabilising covers 10 are used according to the invention, for providing a stability, a coaxiality and the stiffness of the system during compression under high pressure. For this purpose, the chamber is placed in the stabilising covers 10 so that the stabilising flanges 3 entered into the seats 11 and then the whole is placed between the pistons of the press and pressed. The force applied to the stabilising covers 10 is transferred by using the electrode 1 onto the examined powdery sample 6 resulting in its pelletising.

Thanks to the special construction of the stabilising covers 10 it is possible to withdraw the electrical contact 13 allowing for carrying out the measurement of the electrical properties during compression in the press. The electrical contact 13 has a form of a flat plate of a shape matching to the shape of the seat 11 and covers completely its bottom. An exact matching of the shape of the contact 13 and its uniform thickness are extremely important for keeping the stability of the chamber A during compression. The electrical contact 13 is placed between the stabilising flange 3 of the electrode 1 and the bottom of the seat 11. Withdrawing of the contact is possible thanks to the recess 12 in the walls surrounding the seat 11.

The application of layers of the electrical insulator 14 on the surface of the stabilising cover 10 opposite to the surface with the seat 11 is necessary for complete isolation from each other the electrodes 1. The lack of layers of the electrical insulator 14 would result in the short circuit of the electrodes 1 through the metal elements of the press. The layer of the insulator 14 placed inside of the seat 11 could reduce the stability of the chamber during compression in the press.

The determination of the pressure applied on the pressed sample 6 can be carried out in two ways: by calculating the amount of the pressure based on known the amount of pressure of the press pistons and the area of the active surface 2 of the electrode 1 or using additional the measurement pressure system 15. This calculation method of the effective pressure applied on the sample is very simple and non-costly method, although burden with some uncertainty resulting from a low precision of the systems measuring the amount of pressure of the press. The application of the additional pressure measurement system 15 allows for precise determination of the pressure applied on the examined sample 6. The system 15 is arranged between the electrical contact 13 and the bottom of the seat 11 of the stabilising cover 10 or is an integral element of the cover 10. For keeping the stability of the whole system, the element of the system 15 remaining in an indirect contact with the stabilising flange 3 should provide the parallelism of the active surfaces 2 of the pressed electrodes 1.

Carrying out the measurements of the electrical properties by using the chamber according to the present invention, in the variant for multiple use, allows for the monitoring of the compression degree of the tested sample and carrying out the measurements in the function of the pressure also without necessity of using the press. This aim is achieved by means of the compression installation presented in the FIG. 9 and FIG. 10. Utilizing the compression system allows for compression of the powder samples placed in the chamber between the electrodes, controlling of the compression degree and carrying out the measurements of the electrical properties in the function of the pressure without necessity of using the press. It considerably reduces the costs of the carried out measurements. Value of the applied pressure can be calculated knowing the amount of pressure and the surface area of the electrodes or using additional pressure measurement system.

Figure 9:
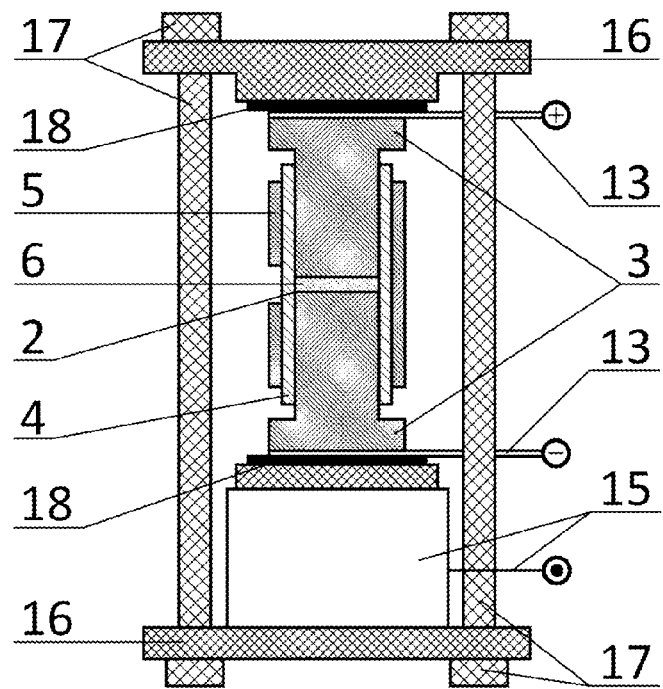
Figure 10:
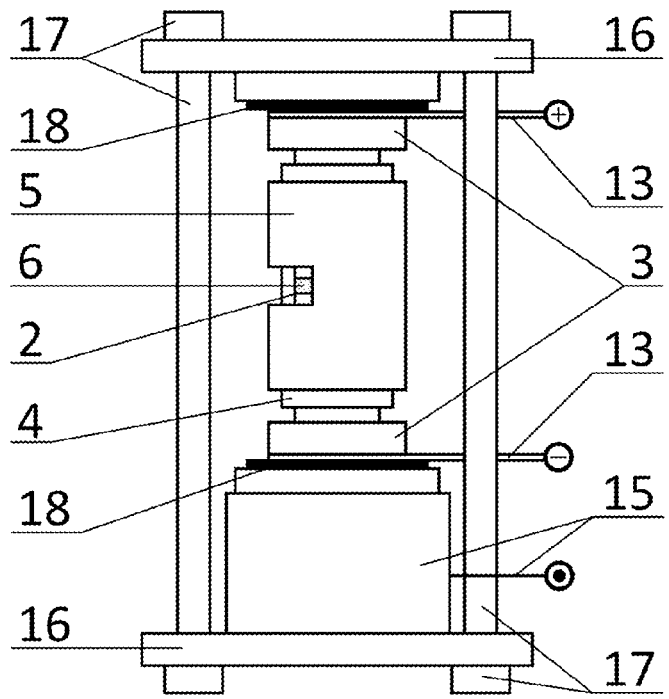

In the FIG. 9 the chamber in the compressing plates 16 is presented in the vertical section along the diameter of the electrodes 1 whereas in the FIG. 10—in the side view. In the indicated figures of the drawing, the chamber has the additional clamping installation containing the compressing plates 16 connected with each other by using the screws 17. The surface compression cover 16 directed towards the flange 3 of the electrode 1 is covered by the layer of the electrical insulator 18 wherein between the stabilising flange 3 of the electrode 1 and the layer of the electrical insulator 18 the electrical contact 13 is arranged, preferably in the form of the flat plate. Between the compressing plates 16 and the stabilising flange 3 of the electrode 1 a system for the measurements of the pressure 15 applied on the sample is also arranged, preferably based on the application of the piezoelectric element.

The clamping installation is used for compression of the powder samples and for carrying out the measurements of the electrical properties in the function of pressure, when the application of the press and the stabilising covers 10 is impossible. The chamber is placed between the compressing plates 16, which are connected to each other by using the screws 17. High pressure is obtained by uniform tighten up the screws 17 resulting in reduction of the distances between the compressing plates 16 and the force is transferred through the electrodes 1 onto the examined sample 6.

The electrical contact 13 in the form of the flat plate is placed between the stabilising flange 3 of the electrode 1 and the stabilising cover 16. The uniform thickness of the electrical contact 13 is extremely important for keeping the stability of the chamber during compression of the plates 16.

The surface of the compression plate 16 remaining in the contact with the chamber is coated with the layer of the electrical insulator 18. The application of layers of the electrical insulator is necessary for complete isolation from each other of the electrodes 1. The lack of layers of the electrical insulator 18 would result in the short circuit of the electrodes 1 through the compressing plates 16 and the screws 17. For keeping the stability of the whole system, the thickness of the layer of the electrical insulator 13 should be uniform.

The measurement of the pressure applied on the pressed sample 6 is carried out using additional system 15 for the pressure measurement. It allows to precise determination of the pressure applied on the examined sample 6. The system 15 is arranged between the electrical contact 13 and the surface of the compression plate 16 or it is an integral element of the cover 16. For keeping the stability of the whole system, the element of the system 15 remaining in indirect contact with the stabilising flange 3 should provide parallelism of the active surfaces 2 pressed of the electrodes 1.

Figure 11:
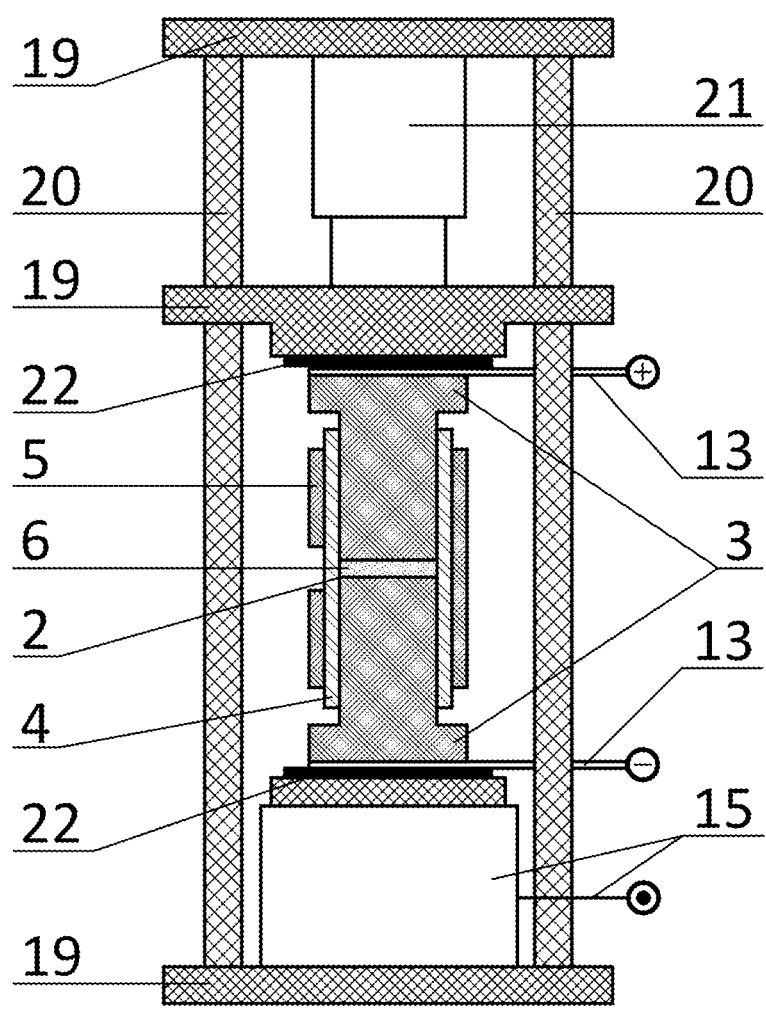
Figure 12:
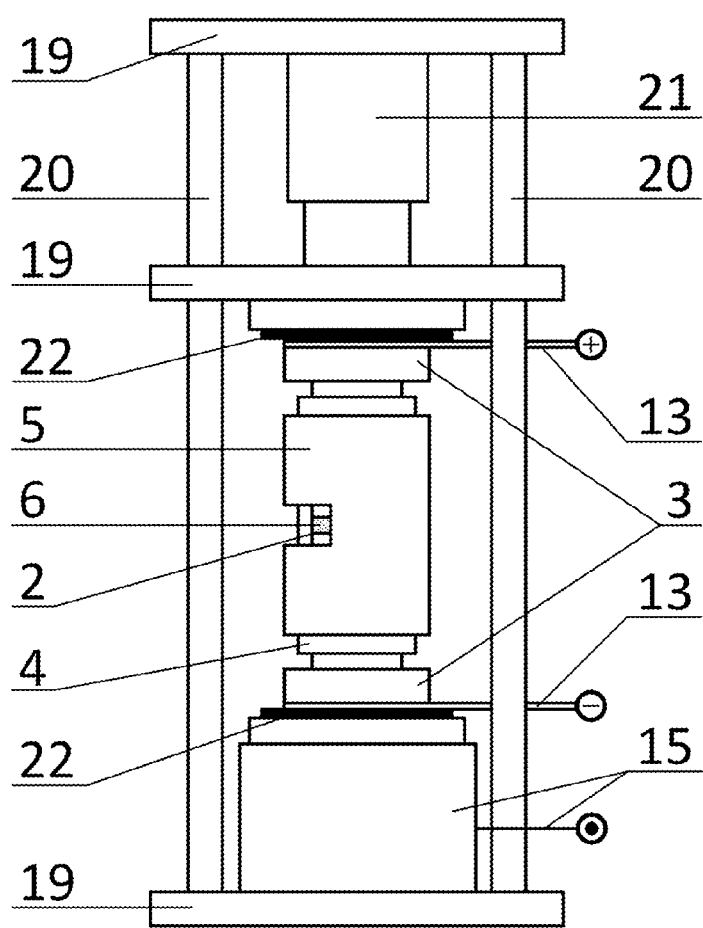

Carrying out the measurements of the electrical properties in the function of pressure by using the chamber according to the present invention, in the variant for multiple use, is possible by using an automatic compression system presented in the FIG. 11 and FIG. 12. Compression of the powder samples 6 placed in the chamber between the electrodes 1 is realized through the application of three parallel compressing plates 19 mounted on the parallel guides 20. Two terminal covers 19 are fixed, whereas the middle cover moves over the guides 20. The multiple use chamber is placed between two covers 19 and then the movable cover is pressed down by using the hydraulic actuator 21 coupled with the pressure measurement system 15.

In the FIG. 11 the chamber in the compressing plates 19 is presented in the vertical section along the diameter of the electrodes 1 whereas in the FIG. 12—in the side view. In the indicated figures of the drawing, the chamber has the additional clamping installation containing three parallel compressing plates 19 mounted on the guides 20 wherein two terminal covers 19 are permanently connected with the guides 20 and the middle cover 19 can be moved along the guides 20. The surface of the compression plate 19 directed towards the flange 3 of the electrode 1 is covered by the layer of the electrical insulator 22 wherein between the stabilising flange 3 of the electrode 1 and the layer of the electrical insulator 22 the electrical contact 13 is arranged, preferably in the form of the flat plate. Between the compressing plates 19 and the stabilising flange 3 of the electrode 1 the system for the measurements of the pressure 15 applied on the sample is also arranged, preferably based on the application of the piezoelectric element.

The clamping installation is used for compression of the powder samples and carrying out the measurements of the electrical properties in the function of precisely controlled pressure. The chamber is placed between the compressing plates 19 seated on the guides 20. High pressure is obtained thanks to the application of the hydraulic actuator 21 that generates the reduction of the distances between the compressing plates 19 and the force is transferred through the electrodes 1 onto the examined sample 6.

The electrical contact 13 in the form of the flat plate is placed between the stabilising flange 3 of the electrodes 1 and the stabilising cover 19. The uniform thickness of the electrical contact 13 is extremely important for keeping the stability of the chamber during compression of the plates 19.

The surface of the compression plate 19 remaining in the contact with the chamber is coated with the layer of the electrical insulator 22. The application of layers of the electrical insulator is necessary for complete isolation from each other of the electrodes 1. The lack of layers of the electrical insulator 22 would result in the short circuit of the electrodes 1 through the compressing plates 19 and the guides 20. For keeping the stability of the whole system, the thickness of the layer of the electrical insulator 22 should be uniform.

The measurement of the pressure applied on the pressed sample 6 is carried out using the additional system 15 for the pressure measurement. It allows to precise determination of the pressure applied on the examined sample 6. The system 15 is arranged between the electrical contact 13 and the surface of the compression plate 19 or it is the integral element of the covers 16. For keeping the stability of the whole system, the element of the system 15 remaining in the indirect contact with the stabilising flange 3 should provide parallelism of the active surfaces 2 pressed of the electrodes 1.

Figure 13:
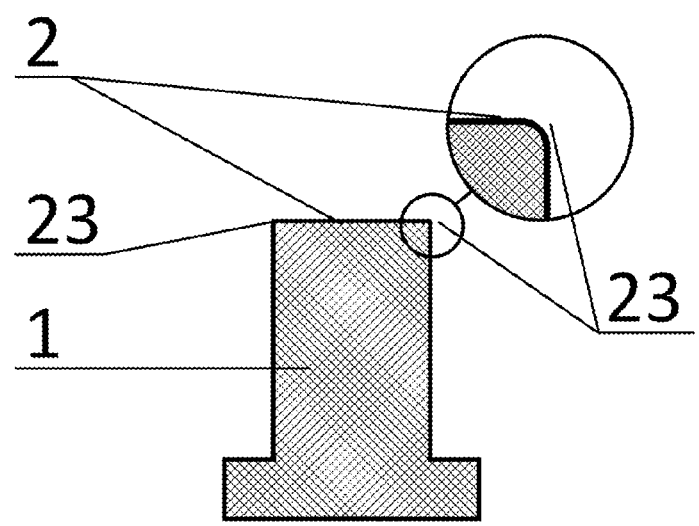

The shape of the electrodes used in the chamber according to the present invention is presented in the FIG. 13. The application of rounded edges allows for carrying out the measurements under increased pressure without the risk of a breakdown of the cylinder made of the insulating material 4 that would result in a puncturing of the system and would also reduce the risk of the short circuit of the electrodes 1 during compression of the chamber under high pressure. Thanks to the application of the stabilising flanges, the whole system gains greater stability during compression under high pressure. The additional purpose of introducing of the stabilising flanges 3 is to make the process of the opening of the chamber after the end of the measurement more easy.

In the FIG. 13 the electrode 1 used in the chamber is presented in the vertical section along the diameter of the electrode. The electrode 1 has a form of a cylinder with the active surface 2 directed towards the interior of the chamber and the additional stabilising flange 3 at the opposite end. The electrode 1 has rounded edges 23 of the active surface 2.

The electrode 1 has the cylindrical shape due to the simplicity of the construction, easiness of the utilization and the resistance for the deformation causing by the application of the high pressure. The electrode 1 has a special stabilising flange 3. Thanks to such construction the chamber is stable during the step of pelletising and it is easier to keep the parallelism of the active surfaces 2 of the electrodes 1 during carrying out the measurement.

The edges 23 of the active surface 2 of the electrode 1 have rounded shape. Thanks to the application of such solution, the edges of the electrode 1 present inside of the chamber are not sharp, allowing for elimination of the risk of puncturing of the thin-walled cylinder 4 made of the insulating material. The application of the rounded edges 23 reduces also the risk of the short circuit of the electrodes 1 during the compression step and during carrying out measurements of the electrical properties pod increased pressure. The additional purpose of utilization of the rounded edges 23 of the electrode 1 directed towards the interior of the chamber is to make the process of the chamber assembling more easy.

Figure 14:
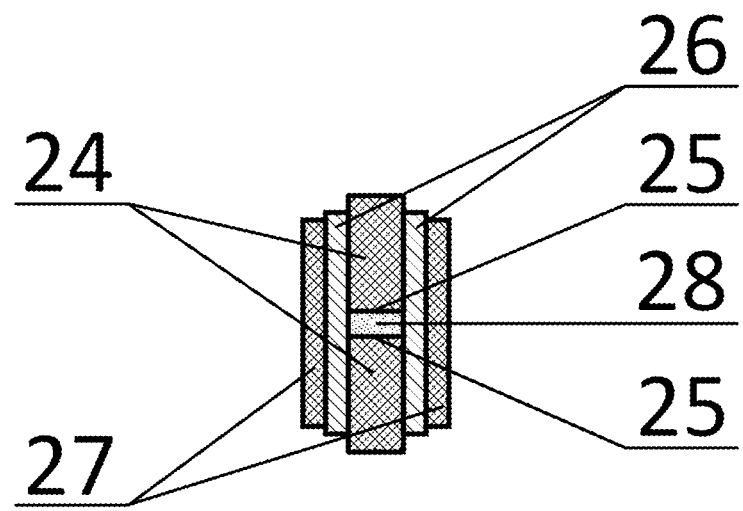
Figure 15:
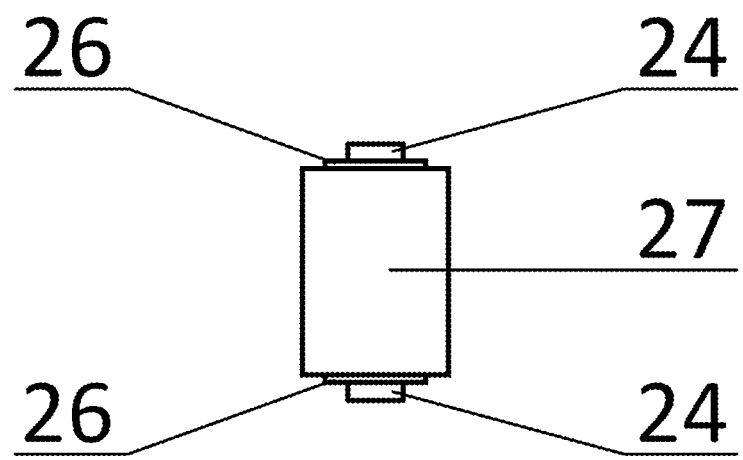

The chamber according to the present invention in the variant for single use only, illustrated in the FIG. 14 and FIG. 15, is a miniaturised version of the chamber according to the present invention in the variant for multiple use. The application of the single use chamber allows for omission the steps of pelletising and deposition of the electrical contact on the pellet by sputtering. According to the invention, the reactive powdery sample is placed directly between the electrodes forming the structural component of the chamber according to the present invention. It allows for current monitoring of the compression degree of the samples and possible increase of the pressure in order to better compression and elimination of the resistance at the boundary of the grains.

Thanks to the small sizes of the single use chamber according to the present invention it is possible to fill it up and hermetic closure inside the glove box filled with the inert gas, which provides the lack of the contact of the samples with oxygen and atmospheric moisture. After closure of the chamber, the whole chamber with the samples directly between the electrodes is pressed in the glove box or outside it. The compression permanently deforms the single use chamber, additionally sealing it. The step of the measurement is carried out de facto in the inner atmosphere thanks to the hermetic closure of the chamber according to the present invention. Thanks to the application in the construction of the chamber according to the present invention of the chemically inert materials the risk of damage of the reactive samples considerably decreases, and in the most of cases is practically eliminated.

The use of the chamber according to the present invention in the variant for single use only allows significantly reduce the costs of the carried out measurements of the electrical properties due to the elimination of the step of the deposition of the electrical contact on the tabletted powdery sample by sputtering, carried out in the expensive sputter coaters. Simultaneously the construction of the chamber according to the present invention is very simple and has the small sizes which reduce the costs of their production, thus additionally reduce the costs of carrying out the measurements of the electrical properties of the solid powder samples.

In the FIG. 14 the single use chamber is presented in the vertical section along the diameter of the electrodes 24 whereas in the FIG. 15—in the side view. The chamber has two cylindrical electrodes 24 coaxially arranged, slidingly and strictly in the thin-walled cylinder 26 made of the insulating material providing the electric insulation, surrounded by the stiffening ring 27. The electrodes 24 take the form of the cylinders with the active surface 25 directed towards the interior of the chamber. Between the active surfaces 25 of the electrodes 24 the sample 28 is arranged. A sum of lengths of the electrodes 24 exceeds the length of the cylinder made of the insulating material 26 and length of the stiffening ring 27 by 5-30%. The height of the cylinder 26 is larger than the length of the stabilising ring 27.

The electrodes 24 are made of soft and chemically inert metal, preferably of acid resistant steel. In the case of carrying out the measurements of the reactive samples, the metal must be chemically inert so as to not react with the tested reactive sample 28 with which electrodes 24 have direct contact. The application of the soft metals allows to easy deforming of the chamber under relatively low pressure, allowing for easy compression of the sample 28 between the electrodes 24 and additionally sealing the chamber. For the deformation of the chamber usually the pressure of the order of 0.8 GPa (the pressure of 1 tone at the diameter of the electrodes of 2 mm) is enough. Such pressure can be obtained by using common laboratory pelleting machine, which is routinely used for compression of the pellets of KBr for the spectral measurements in infrared (pressure up to 15 ton).

The electrodes 24 can be moved slidingly and coaxially inside the thin-walled cylinder 26 made of the insulating material providing the electric insulation. The application of the cylinder 26 is the necessary condition for the hermetic closure of the examined sample 24 inside the chamber according to the present invention. The cylinder 26 must be the electrical insulator so as not to lead to a short circuit of the electrodes 24. In the case of carrying out the measurements of the reactive samples, the cylinder 26 must be made of the chemically inert material so as to stay neutral in relation to reactive powder samples, which have direct contact with.

The cylinder 26 is arranged inside of the stiffening ring 27 which provides the stiffness to the single use chamber during compression. Maintaining of the stiffness of the system allows keeping coaxiality of the electrodes 24 and the parallelism of their active surfaces 25 between which the tested sample 28 is pressed. The cylinder 26 is longer that the stiffening ring 27 by 5-20%, preferably 5-10%, it eliminates the risk of the short circuit of the electrodes 24 during compression of the chamber and during carrying out the measurement.

The measurement of the tested layer thickness of the powdery sample 28 that is pressed between the active surfaces 25 of the electrodes 24 is carried out after completion of the measurement and opening the chamber. The measurement of the thickness of the sample layer 28 is carried out using the precise measurement tool, for example the slide caliper. The single use chamber is opened by cutting it out vertically along the diameter of the electrodes. Thanks to the use of soft metal alloys to the construction of the chamber, it is possible to cut it using conventional tools.

Thanks to the small sizes of the single use chamber only, it is possible to carry out the measurements of the electrical properties for very small samples weighting no more than 2 mg. Thanks to the miniaturisation of the chamber; it is possible to carry out an universal examination of expensive and rare samples.

As mentioned above, the chamber according to the present invention in the variant for single use only needs compressing, thanks to which the tested sample is tableted directly between the electrodes and the chamber alone, is sealed. Compression of the chamber is carried out using additional stabilising holder and the system for compression in the press, presented respectively in the FIG. 16 and FIG. 17. According to the invention it is possible to control of the amount of the pressure applied on the examined powdery sample and to control of the degree of its compression.

Figure 16:
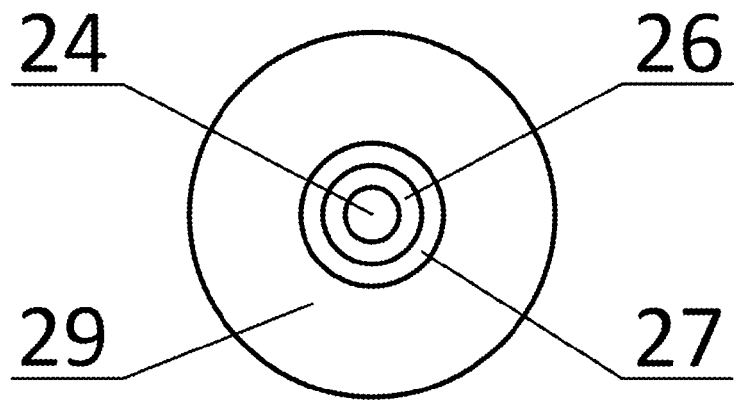

In the FIG. 16 the single use chamber in the flexible stabilising holder 29 is presented in the top view. The electrodes 24 are placed coaxially in the cylinder 26 surrounded from the outside by the stiffening ring 27. The whole single use chamber is placed coaxially in the stabilising holder 29.

Figure 17:
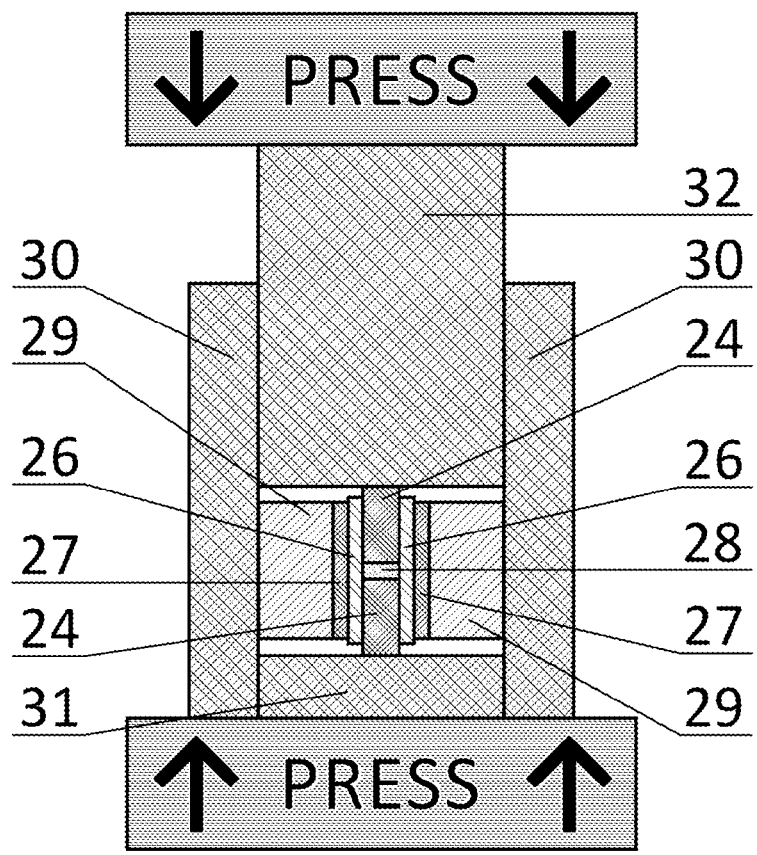

In the FIG. 17 the single use chamber in the stabilising holder 29 and in the compression system is presented in the vertical section along the diameter of the electrodes 24 with indication of the direction of the pressure of the press pistons. The chamber further comprises the flexible stabilising holder 29 and the system for compression in the press, consisting of the thick-walled cylinder 30 the blanking plug 31 and the piston 32.

Thanks to the matching of the size of the opening in the stabilising holder 29 to the size of the closed single use chamber only, the chamber is effectively stabilised in the vertical position, allowing for correct compression of the chamber. The correct compression of the chamber is also promoted by the exact matching of the size of the opening of the thick-walled cylinder 30 to the outer sizes of the stabilising holder 29. The piston 32 is moved strictly and slidingly inside of the cylinder 30 so that it is provided the parallelism of its surface in relation to the base, which allows for correct compression of the single use chamber. The application of the movable blanking plug allows for easy and convenient withdrawing of the pressed chamber from the cylinder 30.

Thanks to the application of the metal alloy with high hardness to the construction of the system for compression of the single use chamber in the press, consisting of the cylinder 30 the plug 31 and the piston 32, this system is characterised by high resistance against applied high pressure. Thanks to the high resistance, this system can be utilised repeatedly for compression of the single use chamber without damages caused by the application of the high pressure.

Thanks to the application of the flexible material to the construction of the stabilising holder 29, the single use chamber can be easily deformed sideways, which generates its additional seal. In the case of insufficient compression of the chamber, it can be placed again in the flexible stabilising holder 29 without any problems and the compression step can be repeated by using the system for compression in the press.

Figure 18:
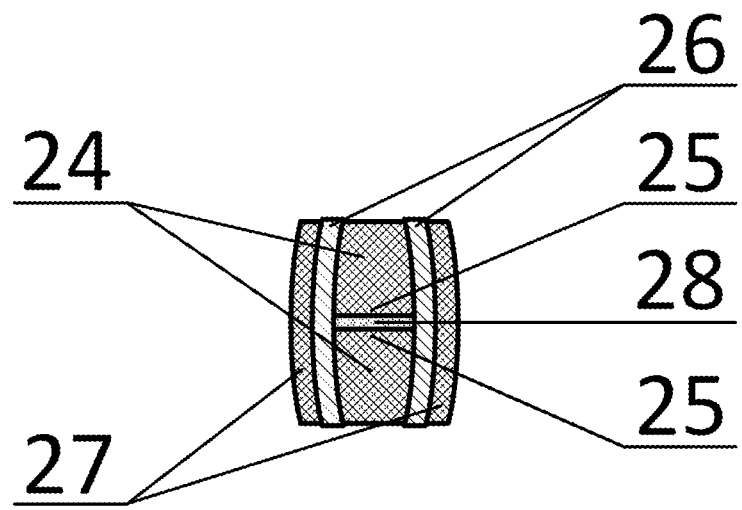
Figure 19:
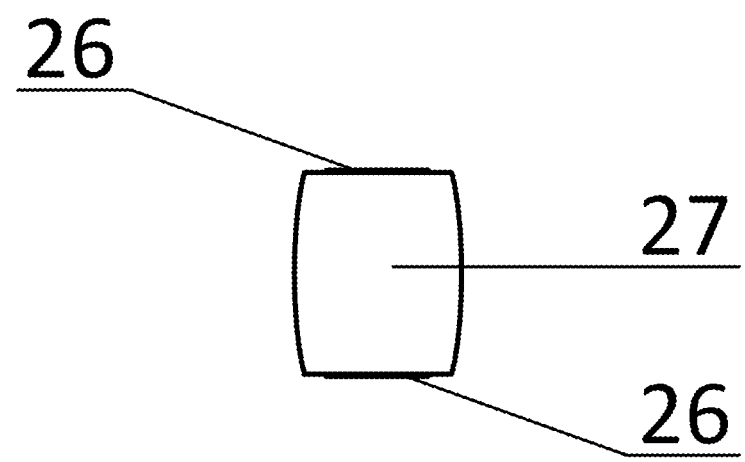

The chamber according to the present invention in the variant for single use only is illustrated in the FIG. 18 and FIG. 19 in the state after completion of the compression. The compression of the chamber allows for permanent closure of the chamber and additionally provides its leak tightness. It is also possible to monitor of the compression degree of the samples currently and in case of need to carry out the compression again, under increased pressure, in order to obtain better compression and to eliminate the resistance at the boundary of the grains.

In the FIG. 18 the single use chamber after completion of the compression is presented in the vertical section along the diameter of the electrodes 24 whereas in the FIG. 19—in the side view. The chamber has two pear-shaped deformed electrodes 24 placed in arc wise deformed thin-walled cylinder 26 made of the insulating material, providing the electric insulation, surrounded by deformed arc wise stiffening ring 27. The electrodes 24 have the active surface area 25 directed towards the interior of the chamber. Between the active surfaces 25 of the electrodes 24 the sample 28 is arranged. After completion of the compression of the single use chamber only, the sum of lengths of the electrodes 24 is equal to the lengths of the stiffening ring 27. The length of the cylinder 26 made of the insulating material is greater than the length of the stiffening ring 27.

Thanks to the application of the soft metal alloy to the construction of the single use chamber only, it is easily subjected to the deformation resulting in its additional seal. Originally, before the compression, the sum of the lengths of the electrodes 24 was larger than both the length of the cylinder 26 made of the insulating material and the length of the stiffening ring 27. Thanks to it, during the compression the material forming the electrodes 24 could be pressed sideways into pear-shaped form inside the single use chamber by compression of the sample 28 between the active surfaces 25. As a result of this pear-shaped deformation of the electrodes 24 the walls of the chamber were pushed out sideways giving characteristic barrel shape.

The application of the cylinder 26 made of the insulating material of the length greater than the length of the stiffening ring 27 results in the reduction of the risk of the short circuit of the electrodes during the compression of the single use chamber. The cylinder 26 is made of flexible and elastic material, which under pressure returns partially to the previous shape. While the metal elements of the chamber (the electrodes 24 and the stiffening ring 27) undergo to the permanent deformation gaining the equal height, the cylinder 26 made of the insulating material partially return to the previous shape. The cylinder 26 returning to the previous shape gains the greater height than the height of the electrodes 24 and the stiffening ring 27 forming characteristic flange between them. The formation of the flange made of the insulating material between the electrodes 24 and the stiffening ring 27 reduce the risk of the short circuit of the electrodes.

Figure 20:
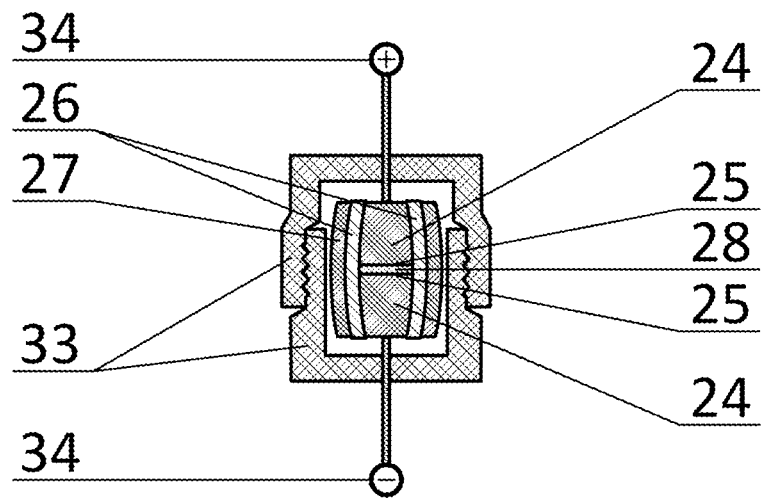
Figure 21:
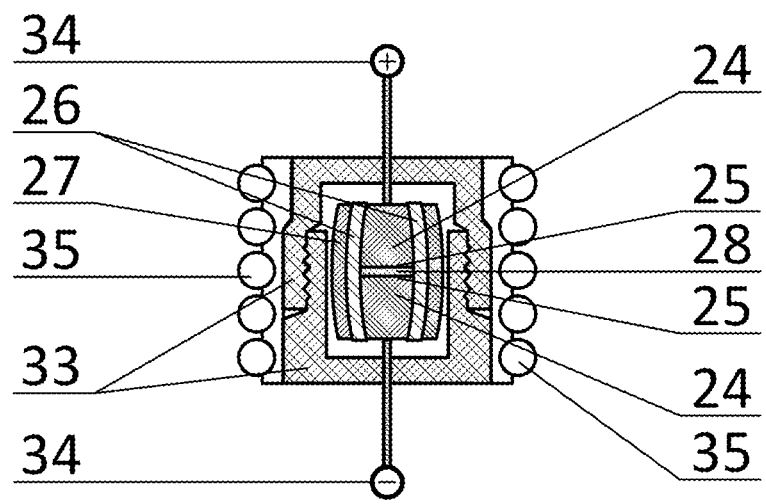

It is possible to carry out of the measurements of the electrical properties in the function of temperature using the chamber according to the present invention in the variant for single use only with the additional hermetic housing illustrated in the FIG. 20 and FIG. 21. According to the invention it is possible to stabilise and regulate temperature by using the additional stabilising temperature system.

In the FIG. 20 the single use chamber placed inside of the hermetic housing 33 is presented in the vertical section along the diameter of the electrodes 24. In the FIG. 21 the single use chamber placed inside of the hermetic housing 33 surrounded by the temperature stabilising and regulating system 35 is presented in the vertical section along the diameter of the electrodes 24. The single use chamber further comprises two-piece, hermetic housing 33 containing the electrical contacts 34. The chamber further comprises the temperature stabilising and regulating installation 35 placed around the hermetic housing 33. The temperature stabilising and regulating system 35 has a form of the coil pipe multiply surrounding the hermetic housing 33.

Thanks to the matching of the size of the hermetic housing 33 to the sizes of the pressed single use chamber only, it may take only a coaxial position inside of the hermetic housing 33. The insertion of the electrical contacts 34 inside of the hermetic housing 33 allows outputting an electrical signal from the single use chamber only in effective and repeatable manner. Thanks to the leak tightness of the hermetic housing 33 and the electrical contacts 34 withdrawn from the housing, it is possible to carry out the measurements once the loaded housing 33 is placed in different media, e.g. in the fluid containers or in the ovens.

Thanks to providing the hermetic housing 33 with the temperature stabilising and regulating installation 35 it is possible to carry out of the measurements of the electrical properties in the function of temperature. The temperature stabilising and regulating system has preferably form of the electric heater, the thermostated fluid tank, the oven or the coil pipe multiply surrounding the hermetic housing 33 connected with the outside thermostat such that the medium of a desired temperature flows through the coil pipe. In the variant utilizing the coil pipe, connected with the outside thermostat or thermostated fluid tank, the temperature in very wide range, depending only on the used medium can be obtained, e.g. the use of ethylene glycol allows to obtain the temperature in the range from −30° C. to +190° C., and the use of diethyl ether gives the range of temperatures from −110° C. to +25° C. The temperature may also be determined based on the measurement of the medium temperature.

Figure 22:
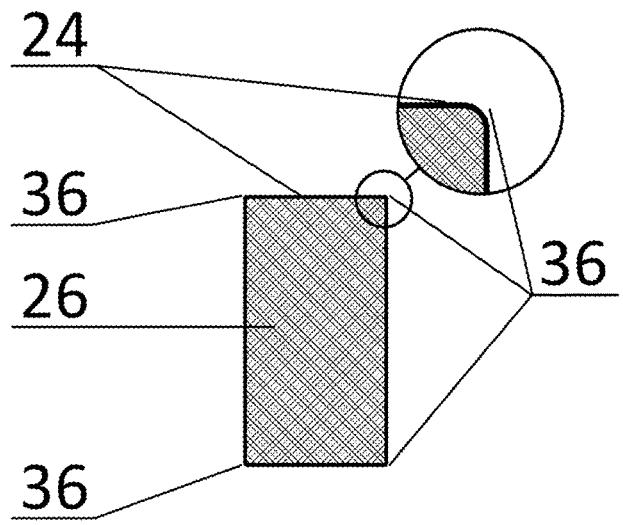
FIG. 22 illustrates the shape of exemplary electrodes used in a single use chamber embodying features of the present invention.

The shape of the electrodes used in the single use chamber only according to the present invention is illustrated in the FIG. 22. The application of rounded edges allows for carrying out the measurements under increased pressure without the risk of a breakdown of the cylinder made of the insulating material that would result in a puncturing of the system. The application of construction according to the present invention reduces also the risk of the short circuit of the electrodes during the compression of the chamber under high pressure.

In the FIG. 22 the electrode 24 used in the single use chamber only is presented in the vertical section along the diameter of the electrode. The electrode 24 has a form of a cylinder with the active surface 25 directed towards the interior of the chamber B. The electrode 24 has rounded all edges 36.

The electrode 24 has the cylindrical shape due to the simplicity of the construction and easiness of the utilization. All edges' 36 of the electrode 24 have rounded shape. Thanks to the application of such solution, the edges of the electrode 24 present inside of the single use chamber only, are not sharp, allowing for elimination of the risk of puncturing of the thin-walled cylinder 26 made of the insulating material and reduction of the risk of the short circuit of the electrodes 24 during the step. The application of the rounded outer edges effectively prevents damage of the cylinder 26 during the compression step, what would result in the formation of the electrical breakdown between the electrode 24 and the stiffening ring 27.

The additional purpose of the application of the rounded, edges 32 of the electrode 20 directed towards into the interior of the chamber B is to make the process of the chamber assembling more easy.

The active surfaces 2 and 25 of the electrodes 1 and 24 in both variants of the chamber according to the present invention may be additionally modified.

During carrying out the measurements of the particularly reactive samples, the active surfaces of the electrodes may be coated by thin layer of chemically inert compound for excluding the risk of chemical reaction between the tested sample and the material the electrode is made of. However, care must be taken considering the thickness of the layer modifying the surfaces of the electrodes that should be so thin that it could conduct electrical current (for example an effect of current tunnelling). The surface area of the electrode may be isolated from the tested sample by for example perfluorinated polymers, preferably FEP or PTFE. It is also possible to passivate the surface of the electrode to form the thin layer of e.g. metal oxide, the metal the electrode is made of. It is also possible to coat the electrodes with the layer of diamond doped with boron (BDD). Other surface modifications are also possible, for example self-organization method by using chemically inert functional groups.

With a completely other reasons, the active surfaces of the electrodes may be coated by the thin layers of the specified metals. During the measurements of the samples having ionic conductance, a very important experiment aimed at identification of the conducting ion is a repetition of the measurements by using the electrodes made of the same metal as conducting ions. In the chamber according to the present invention it is possible to coat the active surfaces of the electrodes with thin layers of different metals.

The chamber according to the present invention was laboratory tested in both variants of the solution. The very reactive samples with extreme properties—from very strong reducing agents to very strong oxidising agents were successfully tested.

By using the chamber according to the present invention in the variant for multiple use, the properties of very strong reducing agents—amidoboranes of alkaline metals (K. Fijalkowski, R. Jurczakowski, W. Koimiriski, W. Grochala, Physical Chemistry Chemical Physics, 14 (2012) 5778-5784) were successfully tested. Amidoboranes are compounds very sensitive to contact with oxygen and atmospheric moisture. During carrying out the measurements, the reaction of the samples being present inside of the multiple use chamber with oxygen or moisture was not observed.

Figure 23:
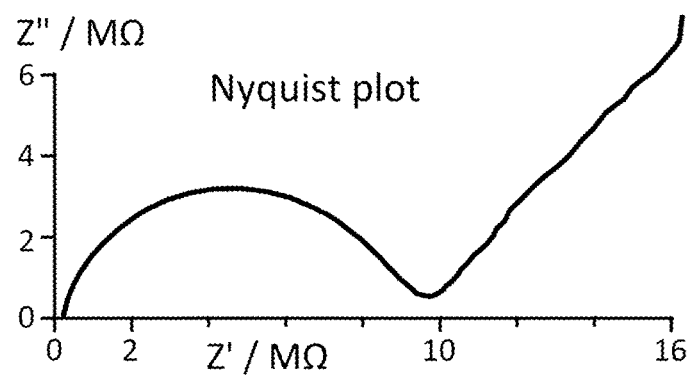
FIG. 23 illustrates results of exemplary impedance measurements obtained by using an exemplary prototype of multiple use chamber embodying features of the present invention.
Figure 23:
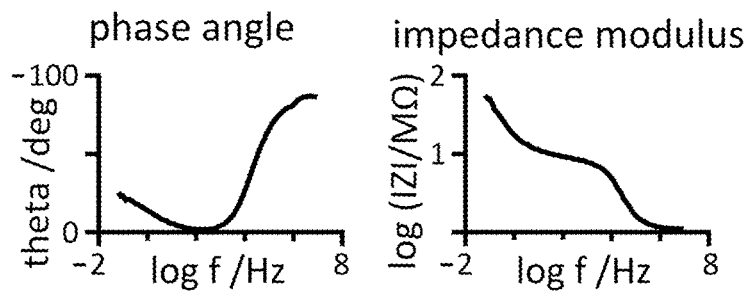

The FIG. 23 shows exemplary results of the impedance measurements obtained by using a prototype of the multiple use chamber according to the present invention for lithium amidoborane, this substance is characterised by high reactivity and shows strong reducing properties. The drawings illustrate Bode plots of a phase angle, a module of an electrical impedance and Nyquist plot of the electrical impedance. The sample showed typical course that is characteristic for the ionic conductors. Recorded impedance spectrum has classic course.

The properties of very strong oxidising agents—the compounds containing $Ag^{2+}$ ions (P. J. Malinowski, M. Derzsi, R. Jurczakowski, Z. Mazej, W. Grochala, thesis in progress—publication planned in 2013) were tested by using the prototype of the chamber according to the present invention in the variant for single use only. The compounds of silver in the oxidation state of +2 are very sensitive to contact with oxygen and atmospheric moisture and during the contact with these substances decompose immediately into the compounds of silver in the oxidation state of +1. During carrying out the measurements in the chamber according to the present invention no changes suggesting decomposition of the tested compounds under influence of oxygen and atmospheric moisture were observed.

Figure 24:
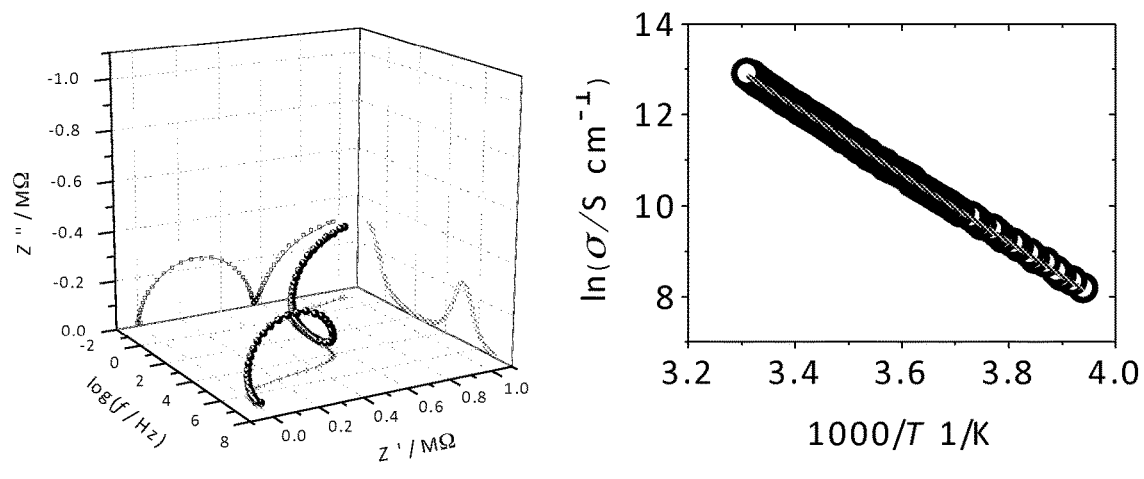
FIG. 24 illustrates exemplary impedance spectrum recorded for samples of silver(II) sulphate, using features of the present invention.

The FIG. 24 illustrates the exemplary impedance spectrum recorded for the samples of silver(II) sulphate. In the complex space in the Nyquist plot, the formation of two semicircles related to the presence of different time constants for a conductivity of the solid phase of $AgSO_4$ and the boundary of the grains of that semiconductor is visible. From the temperature relationship of the conductivity of the solid phase, i.e. at high frequencies, an energy gap for the samples of $AgSO_4$, $E_g=1.24\pm0.05$ eV was determined.

Example of Embodiment

The chamber according to the present invention in the variant for multiple use was embodied using the alloy of the acid resistant steel and the hardened steel as material to the construction of the electrodes 1 and the stiffening ring 5 and a tube made of FEP and PTFE as the cylinder 4 made of the insulating material. The diameter of the active surface 2 of the electrode 1 was 10 mm. The diameter of the stabilising flange 3 of the electrode 1 was 16 mm and its thickness was 4 mm. The electrode 1 had the height of 20 mm, and the thickness of the stabilising flange 3 of the electrode 1 was 2 mm. The cylinder 4 made of the insulating material had the length of 30 mm, the outer diameter of 12 mm, and the inner diameter of 10 mm. The stiffening ring 5 had the length of 26 mm, the outer diameter of 16 mm, and the inner diameter of 12 mm. The inspection opening 7 had the height of 5 mm and a width of 12 mm.

The chamber in the variant for multiple use made of the hardened steel containing the cylinder 4 made of FEP was introduced into the glove box filled with argon. The reactive powdery sample 6 of lithium amidoborane was placed into the chamber closed from one side by the electrode 1 and then the second electrode 1 was slid into the chamber, while removing gaseous phase from the spaces between the parallel active surfaces 2 of the electrodes 1. The entire time the compression process was controlled by observing the sample 6 through the inspection opening 7. Then, the closed chamber was removed from the glove box and once it was placed in the stabilising covers 10 the chamber was pressed under the pressure of 0.5 GPa using the laboratory press. Then, the chamber was placed in the temperature stabilising and regulating installation 8 in the form of coil pipe mounted on the silver sleeve 9 and the whole was placed between the compressing plates 16. Once the electrical contacts 13 were assembled, the screws 17 were tighten up additionally compression of the sample 6 between the electrodes 1. The coil pipe 8 was connected to a thermostat and water of a temperature 40° C. was passed through it. Once the electrical contacts 13 were connected to a frequency analyser, a series of the impedance measurements in the temperatures of 40° C., 50° C., 60° C. and 70° C. was carried out. The state of the samples 6 was monitored visually during heating with the observation of the changes of its colour. After completion of the measurements of the electrical properties and disassembling of the compression system and the heating installation, the closed multiple use chamber was transferred into the glove box filled with argon and there opened. The sample 6 in the form of pellet was removed form the measurement chamber and its thickness was measured using the slide caliper. Then, the sample 6 was triturated for the powder and the spectroscopic measurements in infrared and the X-ray measurements of the samples exposed to the temperature and the high pressure were carried out.

The chamber according to the present invention in the variant for single use only was embodied using the alloy of the acid resistant steel and titanium as material to the construction of the electrodes 24 and the stiffening ring 27 and the tubes made of PTFE as the cylinder 26 made of the insulating material. The diameter of the active surface 25 of the electrode 24 was 2 mm. The electrode 24 had the height of 5 mm. The cylinder 26 made of the insulating material had the length of 9 mm, the outer diameter of 2 mm, and the inner diameter of 3 mm. The stiffening ring 27 had the length of 8 mm, the outer diameter of 5 mm, and the inner diameter of 3 mm.

The chamber in the variant for single use only made of the acid resistant steel equipped with the cylinder 26 made of PTFE was placed into the glove box filled with argon. The reactive powdery sample 28 of silver (II) sulphate was placed into the single use chamber closed from one side of the electrode 24 and then the second electrode 24 was slid into the chamber, while removing gaseous phase from the spaces between the parallel active surfaces 25 of the electrodes 24. Then, the closed chamber was removed from the glove box, and placed in the flexible stabilising holder 29 and then in the cylinder 30 closed with a plug 31, pressed down with a piston 32 and pressed under the pressure of 0.5 GPa using of the laboratory press. The pressed single use chamber was removed from the stabilising holder by cutting it out. Then, the pressed chamber in the form of characteristic barrel was placed in the hermetic housing 33 with electrical contacts 34 and subsequently the hermetic housing was placed in the temperature stabilising and regulating installation 35 in the form of thermostated container with water. Once the electrical contacts 34 were connected to frequency analyser, the series of the impedance measurements in the temperatures of 40° C., 50° C., 60° C. and 70° C. was carried out. After completion of the measurements of the electrical properties and opening of the hermetic housing 33, the pressed single use chamber in the form of the characteristic barrel was cut open and the thickness of the sample 28 using the slide caliper was measured. Then, the sample 28 was triturated for the powder and the spectroscopic measurements in infrared and the X-ray measurements of the samples exposed to the temperature and the high pressure were carried out.

LIST OF NUMBER REFERENCES USED IN THE DESCRIPTION OF THE INVENTION AND IN THE DRAWINGS

Chamber According to the Present Invention in the Variant for Multiple Use
1 electrodes
2 active surface of the electrodes (1)
3 stabilising flange of the electrode (1)
4 thin-walled cylinder made of the insulating material
5 stiffening ring surrounding the thin-walled cylinder (4)
6 sample placed between the active surfaces (2) of the electrodes (1)
7 inspection opening formed by the recess in the stiffening ring (5)
8 temperature stabilising and regulating system
9 sleeve, which the temperature stabilising and regulating system (8) is seated on
10 stabilising covers for compressing of the multiple use chamber in the press
11 seat in the surface of the stabilising cover (10) matching to the flange (3)
12 recess in the walls surrounding the seat (11)
13 electrical contact
14 layer of the electrical insulator
15 system for the measurements of the pressure applied to the sample
16 compression plates for compressing the multiple use chamber without use of the press
17 screws connecting the compression plates (16) to each other
18 layer of the electrical insulator
19 compression plates of the system for the automatic pressure regulation
20 rigid guides connected with the compression plates (19)
21 hydraulic actuator
22 layer of the electrical insulator
23 rounded edges of the active surface (2) of the electrode (1)

The Chamber According to the Present Invention in the Variant for Single Use Only
24 electrodes
25 active surface of the electrodes (24)
26 thin-walled cylinder made of the insulating material
27 stiffening ring surrounding the thin-walled cylinder (4)
28 sample placed between the active surfaces (25) of the electrodes (24)
29 flexible stabilising holder for compression of the single use chamber in the press
30 cylinder—the element of the system for compression of the single use chamber in the press
31 blanking plug—the element of the system for compression of the chamber in the press
32 piston—element of the system for compression of the chamber in the press
33 hermetic housing
34 electrical contacts being present in the hermetic housing (30)
35 temperature stabilising and regulating system
36 rounded edges of the active surface (21) of the electrode (20)

The invention claimed is:

1. A measuring apparatus, comprising:
   a. a detachable measurement module, including:
      i. a substantially cylindrical sleeve comprising a substantially insulating material;
      ii. at least two cylindrical electrodes longitudinally spaced apart with respect to one another and coaxially disposed for slidable engagement within the substantially cylindrical sleeve, the at least two cylindrical electrodes including an outer edge coupled to a corresponding flange and a rounded inner edge opposite the outer edge, the rounded inner edge of a first electrode of the at least two cylindrical electrodes configured to be across from the rounded inner edge of a second electrode of the at least two cylindrical electrodes in an arrangement for receiving a sample between the at least two cylindrical electrodes, the at least two cylindrical electrodes and the substantially cylindrical sleeve disposed in intimate contact with one another to substantially exclude entrance of gases external to the measuring apparatus;
      iii. a stiffening ring substantially surrounding the substantially cylindrical sleeve; and
   b. a clamp to receive the detachable measurement module.

2. The apparatus of claim 1, wherein the at least two cylindrical electrodes comprise one or more substantially chemically inert materials.

3. The apparatus of claim 2, wherein the substantially chemically inert material comprises steel, monel, titanium, tungsten, tungsten carbide, titanium-molybdenum alloy, or a combination thereof.

4. The apparatus of claim 1, wherein a surface of the at least two electrodes comprises layer of substantially chemically inert material.

5. The apparatus of claim 4, wherein the substantially chemically inert material comprises metal oxide, polytetrafluoroethylene (PTFE), diamond doped with boron (BDD), or a combination thereof.

6. The apparatus of claim 1, wherein the stiffening ring comprises one or more inspection apertures that extends from an outer surface through to an inner surface.

7. The apparatus of claim 6, wherein the substantially cylindrical sleeve comprises a transparent material or a translucent material.

8. The apparatus of claim 7, wherein the substantially cylindrical sleeve comprises polytetrafluoroethylene (PTFE), perfluorinated ethylene/propylene copolymer (FEP), or a combination thereof.

9. The apparatus of claim 6, wherein a circumferential dimension of the one or more inspection apertures are equal to or less than ⅖ of an outer circumference of the stiffening ring.

10. The apparatus of claim 1, further comprising means for regulating temperature of the detachable measurement module.

11. The apparatus of claim 10, wherein the means for regulating temperature of the detachable measurement module comprises a helical coil.

12. A measurement apparatus, comprising:
 a. a measurement module, including:
  i. a substantially cylindrical electrically insulating sleeve formed from a substantially chemically inert material;
  ii. two removable substantially cylindrical electrodes formed from a material that is easily deformable under an applied force, the removable substantially cylindrical electrodes formed from chemically inert electrically conductive material and being longitudinally spaced apart and coaxially arranged for slidable engagement within the substantially cylindrical sleeve, each electrode comprising an outer edge and a rounded inner edge opposite the outer edge, the rounded inner edge of a first electrode of the two removable substantially cylindrical electrodes configured to be across from the rounded inner edge of a second electrode of the two removable substantially cylindrical electrodes so as to receive a sample between the first and second electrodes; and
  iii. a stiffening ring formed from easily deformable under applied force soft material and surrounding the sleeve;
 b. wherein a length of the sleeve is greater than a length of the ring, and a sum of lengths of the first and second electrodes is greater than the length of the sleeve.

13. The measurement apparatus of claim 12, wherein the substantially cylindrical sleeve is formed from polytetrafluoroethylene (PTFE), perfluorinated ethylene/propylene copolymer (FEP), or a combination thereof.

14. The measurement apparatus of claim 12, wherein the first and second electrodes and the stiffening ring are formed from soft metal alloy.

15. The measurement apparatus of claim 12, wherein a surface of the first and second electrodes comprises a layer of a substantially chemically inert material.

16. The measurement apparatus of claim 15, wherein the substantially chemically inert material comprises metal oxide, polytetrafluoroethylene (PTFE), diamond doped with boron (BDD), or a combination thereof.

17. The measurement apparatus of claim 15, further comprising:
 a. a disposable detachable holder; and
 b. a compression module comprising a metal alloy and having
  i. a walled metal cylinder,
  ii. a plug disposed at one end of the walled metal cylinder, and
  iii. a cylindrical piston disposed at another end of the walled metal cylinder and for slidable engagement with an interior of the walled metal cylinder.

18. The measurement apparatus of claim 12, further comprising a hermetically sealable housing including electrical contacts and a temperature regulating module surrounding the hermetic housing.

19. The measurement apparatus of claim 12, wherein the first and second electrodes comprise substantially rounded edges.

20. The measurement apparatus of claim 12, wherein, in a second configuration, the lengths of the sleeve, the ring, and the sum of the lengths of the first and second electrodes, when configured to accept a sample disposed between the first and second electrodes, are sealed by a permanent deformation under applied force form a substantially air tight chamber.

21. A method for measuring electrical properties of a substantially incompressible fluid sample, comprising:
 a. providing a removable measurement module, including:
  i. a cylindrical electrically insulating sleeve;
  ii. two removable cylindrical electrodes longitudinally spaced apart and coaxially arranged for slidable engagement within the sleeve, each electrode having an outer edge and a rounded inner edge opposite the outer edge, the rounded inner edge of a first electrode of the two removable cylindrical electrodes configured to be across from the rounded inner edge of a second electrode of the two removable cylindrical electrodes for receiving the substantially incompressible fluid sample between, the first and second electrodes and the sleeve together configured to form a substantially air-tight chamber for housing the substantially incompressible fluid sample; and
  iii. a stiffening ring surrounding the sleeve;
 b. opening the module by removing one of the cylindrical electrodes and placing the module in an inert gas atmosphere;
 c. dispensing the substantially incompressible fluid sample into the chamber and closing the module in the inert gas atmosphere by placing the removed electrode into place to form an air-tight chamber;
 d. subjecting the sample to compression to remove a portion of the sample in a gaseous phase from the chamber and to bring about contact of the sample with the cylindrical electrodes;
 e. placing the module into a clamp and coupling the clamp to an electrical analyzer; and
 f. measuring the electrical properties of the sample.

22. The method of claim 21, wherein the sample is in a solid state.

23. The method claim 21, further comprising regulating parameters including temperature, pressure, frequency of electric field variation, time, or a combination thereof.

24. The method of claim 21, further comprising subjecting reactive or air and moisture-sensitive samples to measurements.

* * * * *